(12) United States Patent
Clifford et al.

(10) Patent No.: US 8,476,025 B2
(45) Date of Patent: Jul. 2, 2013

(54) ATM-DEPENDENT PHOSPHORYLATION OF SP1 IS INVOLVED IN THE CELLULAR RESPONSE TO DNA DAMAGE AND ENHANCES CELLULAR SURVIVAL AFTER DNA DAMAGE

(75) Inventors: Jane Clifford, Narberth, PA (US); Beatrix A. Olofsson, Philadelphia, PA (US); Crystal M. Kelly, Columbus, OH (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 12/187,187

(22) Filed: Aug. 6, 2008

(65) Prior Publication Data

US 2009/0081712 A1 Mar. 26, 2009

Related U.S. Application Data

(60) Provisional application No. 60/963,791, filed on Aug. 6, 2007.

(51) Int. Cl.
*G01N 33/53* (2006.01)

(52) U.S. Cl.
USPC .......................................... 435/7.1; 436/518

(58) Field of Classification Search
None
See application file for complete search history.

(56) References Cited

U.S. PATENT DOCUMENTS

2002/0197679 A1* 12/2002 Tang et al. ............. 435/69.1

FOREIGN PATENT DOCUMENTS

WO   WO 2005039645   * 5/2005

OTHER PUBLICATIONS

Iwahori et al. (J Virology 2007, vol. 81, p. 9653-9664).*
Harlow et al. (Antibody Laboratory Manual 1998 Cold Spring Harbor Laboratory, p. 141-155).*
Campbell (Monoclonal Antibody Technology 1986 edition, chapter 1 to section 1.3.4).*
Abraham, 2004, DNA Repair 3:883-7.
Armstrong et al., 1997, J. Biol. Chem. 272:13489-95.
Bartek and Lukas, 2007, Curr. Opin. Cell. Biol. 19:238-45.
Berkovich et al., 2007, Nature Cell Biol. 9:683-90.
Chu and Ferro, 2005, Gene 348:1-11.
Flick et al., 1998, Nature 394:96-101.
Fojas de Borja et al., 2001, EMBO J. 20:5737-47.
Hickson, et al. 2004, Cancer Res. 64:9152-9.
Jackson et al., 1990, Cell 63:155-65.
Kim et al., 1999, J. Biol. Chem. 274:37538-43.
Meighan-Mantha et al., 1999, Mol. Cell Biochem. 199:209-15.
Mirzoeva and Petrini, 2001, Mol. Cell. Biol. 21:281-8.
Muscarella, et al., 1990, Mol. Cell Biol. 10:3386-96.
O'Neill et al., 2000, J.. Biol. Chem. 275:22719-27.
Olofsson et al., 2007, Mol. Cancer Res. 5: 1319-30.
Rogakou et al., 1998, J. Biol. Chem. 273:5858-68.
Rothkamm and Lobrich, 2003, Proc. Natl. Acad. Sci. U.S.A. 100:5057-62.
Ryu et al., 2003, J. Neurosci. 23: 3597-606.
Shiloh, 2006, Trends Biochem. Sci. 31:402-10.
Tibbetts et al., 1999, Genes Dev. 13:152-7.
Traven and Heierhorst, 2005, Bioessays 27:397-407.
Ward, et al. 2001, J. Biol. Chem. 276:47759-62.
Yang et al., 2000, FASEB J. 14:379-90.
Tainer et al., "Defining Antibody-Antigen Recognition: Towards Engineered Antibodies and Epitopes," *Intern. Rev. Immunol.*, 1991, 7:165-188.
Alexander et al., "Altering the antigenicity of proteins," *Proc. Natl. Acad. Sci.*, Apr. 1992, 89:3352-3356.

* cited by examiner

*Primary Examiner* — Jacob Cheu
(74) *Attorney, Agent, or Firm* — Riverside Law LLP

(57) ABSTRACT

The present invention is related to the discovery that phosphorylation of SP1 (SEQ ID NO.: 2) at serine residue 101 (known herein as phosphoserine[101] Sp1) is an important part of a cell's response to DNA damage. This phosphorylation event is important for subsequent Sp1 localization to a site of DNA damage and is correlated with increased cellular viability in response to DNA damage.

5 Claims, 21 Drawing Sheets

```
gtccggcttc gcttgcctcg tcagcgtccg cgttttccc ggccccccc aacccccccg     60
gacaggaccc ccttgagctt gtccctcagc tgccaccatg agcgaccaag atcactccat   120
ggatgaaatg acagctgtgg tgaaaattga aaaggagtt ggtggcaata atgggggcaa   180
tggtaatggt ggtggtgcct tttcacaggc tcgaagtagc agcacaggca gtagcagcag   240
cactggagga ggagggcagg agtccagcc atccccttg gctctgctgg cagcaacttg    300
cagcagaatt gagtcaccca atgagaacag caacaactcc cagggcccga gtcagtcagg   360
gggaacaggt gagcttgacc tcacagccac acaactttca cagggtgcca atggctggca   420
gatcatctct tcctcctctg gggctaccc tacctcaaag gaacagagtg gcagcagtac   480
caatggcagc aatggcagtg agtcttccaa gaatcgcaca gtctctggtg ggcagtatgt   540
tgtggctgcc gctcccaact tacagaacca gcaagttctg acaggactac ctggagtgat   600
gcctaatatt cagtatcaag taatcccaca gttccagacc gttgatgggc aacagctgca   660
gtttgctgcc actggggccc aagtgcagca ggatggttct ggtcaaatac agatcatacc   720
aggtgcaaac caacagatta tcacaaatcg aggaagtgga ggcaacatca ttgctgctat   780
gccaaaccta ctccagcagg ctgtcccct ccaggcctg gctaataatg tactctcagg    840
acagactcag tatgtgacca atgtaccagt ggccctgaat gggaacatca ccttgctacc   900
tgtcaacagc gtttctgcag ctaccttgac tccagctct caggcagtca cgatcagcag   960
ctctggctcc caggagagtg gctcacagcc tgtcacctca gggactacca tcagttctgc  1020
cagcttcgta tcatcacaag ccagttccag ctccttttc accaatgcca atagctactc  1080
aactactact accaccagca acatgggaat tatgaacttt actaccagtg gatcatcagg  1140
gaccaactct caaggccaga cacccagag ggtcagtggg ctacagggt ctgatgctct   1200
gaacatccag caaaaccaga catctggagg ctcattgcaa gcaggccagc aaaaagaagg  1260
agagcaaaac cagcagacac agcagcaaca aattcttatc cagcctcagc tagttcaagg  1320
gggacagcc ctccaggccc tccaagcagc accattgtca gggcagacct ttacaactca  1380
agccatctcc caggaaaccc tccagaacct ccagcttcag gctgttccaa actctggtcc  1440
catcatcatc cggacaccaa cagtggggcc caatggacag gtcagttggc agactctaca  1500
gctgcagaac ctccaagttc agaaccccaca agcccactgag atcaccttag cccaatgca  1560
gggtgttttcc ttgggcaga ccagcagcag caacaccact ctcacaccca ttgcctcagc  1620
tgcttccatt cctgctgcag cagtcactgt gaatgctgct caactctcct ccatgccagg  1680
cctccacacc attaacctca gtgcattggg tacttcagga atccacgtgc acccaattca  1740
aggcctcccg ttggctatag caaatgcccc agctgatcat ggagctcagc ttggtctcca  1800
tgggctggt ggtgatggaa tacatgatga cacagcaggt ggagacgaag agaaaacag    1860
cccagatgcc caaccccaag ccggtcggag gaccggcgg gaagcatgca cctgccccta  1920
ctgtaaagac agtgaaggaa ggggctcggg ggatcctggc aaaaacaaac agcatatttg  1980
ccacatccaa ggctgtggga aagtgtatgg caagacctct cacctgcggg cacacttgcg  2040
ctgcataca ggcgagaggc catttatgtg tacctggtca tactgtggga aacgcttcac   2100
acgttccgat gagctacaga ggcacaaacg tacacacaca ggtgagaaga aatttgcctg  2160
ccctgactgt cctaagcgct tcatgaggag tgaccacctg tcaaaacata tcaagaccca  2220
ccagaataag aagggaggcc caggtgtagc tctgagtgtg gcactttgc ccctggacag   2280
tggggcaggt tcagaaggca gtggcactgc cactccttca gcccttatta ccaccaatat  2340
ggtagccatg gaggccatct gtccagaggg cattgcccgt cttgccaaca gtggcatcaa  2400
cgtcatccag gtggcagatc tgcagtccat taatatcagt ggcaatggct ctgagatca   2460
ggcacccggg ccagagaca tatgggccat accccttaac cccggcatgc aagtagcat    2520
gggtccaaga gacatggaag agagagccat gaagcattaa aatgcatggt gttgagaaga  2580
atcaggagag ggatacaaga gaggatagg ggtcccggca cccatcctta tcatcagtg    2640
ctcttttcaag gtgggaaaca ttagtgaaaa ttctgttggt gccaccgttt gatgagcatt  2700
tgtttgaccc cagtttcttc ttacactcct tacccagcc taccttcct gcatttctct    2760
tctcagctct tccatgatgg attccccccc ctttcctaaa gccatcatgc cttgataaat  2820
atatatcatc attgaaatac ttttttaacaa aaaacagatt ctatattatt atatatatat  2880
atatatatat aaagatatat agagatgcat tcacagggt tggctcggag gaggaagacc   2940
attctgtgac caaaatacct tggtcatttt ttttatattg ccttatttcc ctatggctga  3000
gccttgttgt gacacatcaa gcttttctgt agatgttgtc ttggcttccc accagcttaa  3060
gcgttcatat gctctgcttt tagttcatat atacatacat aatgttttc ctttcttaat   3120
tttgtctttt tgtttgggat cagcttcttg cactccttcc ctaactcaac tgttgccgtc  3180
tcatcttctc tcatctgatc acttcatgtt ttgttttgt tactgctgg atgaggcact    3240
tctgtcaatt ttttcaggac cttagttcca gcagcagaat ggaaaaatcc ttgaagccca  3300
ggctgatgct tgaagtaact gtggagggag tgttcaaaat actactgacg caggcacctt  3360
cttggcgctg gagagtcaaa ggcatctccc ttcattagct gctctgagca tcaagaatta  3420
gaagtctttc agtggaattg tacaagagtc cctttgaaga taataatctt ggctcagttt  3480
gtataaactg tcaaattttc aaataatagg tacggggctt tcactaggaa aatcatgtgc  3540
tcagaacagg aaatgactcg tagtcaggtt cacgagttag tggagtattt ggactttggt  3600
actgtctct tccaaggtag ctctaagttt tgatgtgtgg gcttctgagt ttatattctg   3660
aaaggaaata cacttctttt gaacatcccc actaggttct tttccattgt caataaggag  3720
catcagccag tgaatctgtt tcaggttcc attctgcaga actcctccaa agcatgtgct  3780
```

Figure 16A

```
agtggcaaga cagtggttct tatgatctttt tcccttaact tttccttcta tgttcttggg   3840
tggttcctaa gggaaaggca agcacatgat catgggaatg atagcccaga acaaaaagaa   3900
atcttgtctt accacagtct tttatacgag agattgggag aaatcatcct gttttctctg   3960
tgacctgatt tcagaagaca ctgatccaaa aattataacg gcagggaacc tagtgcattt   4020
ggcactgaga tttaaatgca accagaattg tcctcaaggc ccagccataa aagcattgtc   4080
tctctcgacc ttctggtatc ttgttacaga gcttttcact gtgaggaagt gtggaaaaat   4140
agctctgtgt gtgtgtgtgt gtgtgtctgt gtgtgtgtgt gtaatctctt aggttcggga   4200
taggttttct gctagccaat attaaaagag acctgcaata aaaaaattac cctgatctga   4260
tagaaagcaa gtgttttttct atgtgtcggt gaatgtgtgt tcatgcccgt atatgtctac   4320
acacagatga caaattatat ttgaaatcgt tggaaaataa attcagatca aaatgccttt   4380
caggcccatt acctagaaat ctatcttaaa acctgggtat gttcctaagg tcatttcttt   4440
gcttatgcta aattaattac aattatcaat ggaggatatt ctactgtact ttttaaaaa    4500
gaaactattt ttgtgtttca aagtgaaacc aacatccaga tctatagcag agtccttatt   4560
cttctcataa atcttttttac tttggctaca aatagatgat ggtatgattc tattatatat   4620
tttatataaa atccatccaa attaagtttt gggtaagtgt gttgtttaat ctgaactata   4680
gtaacttaat actctaaaca atagttcact ccatttggtc ctttctccac agatgtaatt   4740
atgttttcaa ctcaggaact atggcaagga acttccccca gatcaaattc tattaacgct   4800
gagatacaag tcatccatcc acagccacta tcataccctt tattctcact gaaagcaga    4860
actcagaacc tgttatttta tgtctgtaat catgtacttt ggcatctttt ggaggaaagg   4920
ggcaggataa ctcactggaa tgtacagtat tttgctagtg catttcaagg aatggaatct   4980
tctccagtat gaaattacca gataaaaat aatgtaatga tgctgagcat ataagctttt    5040
agaaggtaat ttgatggtat ttctttctcg aatgaaagc tgctggttta ccctcaaccc    5100
tattcattag cattaccatg agtgaattta tatctaatta tttccacttg ccctgttctc   5160
ttcacaccaa ggaagctcca gatccagtat cttgtttggc ctcaaaacag aagcagcttc   5220
ttttgtctcc cagcagtagt gagccactca gtctcttcca caggaagttt ggagcctaca   5280
ttccttgagt caggagctta ttacagaaaa accccgtttc cctgaacttt tggctaacag   5340
aaattaattt aactgacatg catattcatt ctgaattttt ttcctaagt ttttttcatt     5400
ttttgaatg agttttttaa atttttaga tgaccaaaac ttgcagggca gggatgccc      5460
agaagagtgg tgagatagta aaacacttat tccctcatcc tttcaggttt tcaggttgcc   5520
catttatatt catttacatg tcatttcact gtctcacttt ttacccacaa cagtaacaac   5580
ccacacogtc ttccttcagg gattttccaac tggcactctg tgggtgctac acagaatgca   5640
atttaatgga tatttctcag cctggttcag aataaattga tcctttgatc ccagaaagta   5700
tatactgaag tgtgggataa agatatatgat tagggagggg ttggagacaa aagctctaaa    5760
ttactatggc tgatttattt ctactatata catatatatt ttttgctttt gtatatccta   5820
tataggaaac taagcattgt atttttttta acaaatctaa aaaagcacta tgaactacag   5880
gtgtttgact ttcaaaatat attttgtatt gttaatatct tcacattctg tgaatactgg   5940
aagctgcaga tcttttgctag gacgcaaaa atttatatac tttttgacgg gttcttctgg   6000
ggtgctaatc aggcccctgt tatgcttagg gggagccctg gtgctacttg cttgaagttt   6060
tcagtgtaag taccctgatg cctttcgac cttgggatca gatcaagagt tttggagatc    6120
aggtaccaag gaaataagca cagtctagct gcctcaagtg aggggcctt tgcatagctc    6180
tccttccccc tcactgaagc tgggtagcct attggggttg agagggaaaa tgtgaaatct   6240
cagaatttat ctcccttaca agagagccag taacttatgt acaaggatga aagaaaggtc   6300
gcagcagtag cttttgggaa agggagcaag atatggcact tctccaaccc cggaaaacat   6360
tgcttttgaa aactgctgat aaaatatgag ccggttatta cttctgtttg ggagactgtg   6420
ctctctgtgg tgcctctctt ggctctactc cacagatacc agacctcttc taagacgatg   6480
agcagaccag ctttgaggtt gaccctgtttc tctttgtctg ccttcccaaa acaccagccc   6540
ccaggaagac attaagcacc cttaagctta aattcctact ccctcttcca aatttcgctc   6600
acttgcctta gatccaagcc agggaaagga aaagaagggg ggtctctcgc tttattactc   6660
ccctaagtct ttactctgac ttcccccaaac ccagaaagat tttctccaca gtgttcattt   6720
gaaagaggag tattttgtcc cattttcccc ttcctcatta tcaaacagcc ccagtcttcc   6780
ttgtctctgc taagaaagta gaggcatgat gatctgcctc tcaactgccc taagtcctag   6840
ctaagtatca ggggaaaaaa aaaaaaaaaa agcctaacaa atgggattag actagcgctg   6900
caagtagtga ggattttgtt gatacctctg ctgggatgtg tgctttccca tatcttgcct   6960
tcaggaatta cactgtgcct tttcccagg gatatgggct ctgtctaccc agtgctccag   7020
tttcccggta actgctcttg aacattctgg acaagggcag gtcttcatat tttgatcat    7080
ccctttctcc cagtgaaatc ccatagccct tacctagagt ctagggcaca aagacttcgg   7140
ggaagataca ctgagattca cctgagcaga catctacaca caccagtcgc agctgcccca   7200
gggcctgctt cccttccta agtcgtcat cctggagga ggatgggtgg tgctccaatc     7260
tctggtgcct aaaaacccaa gtttattcct ctcttaacac tggcaataac cagtccacac   7320
cactgttgcc ttttaaaacc tcttaataat ctcatgctgt gtttgttttg attccaatcc    7380
aattatcacc agggctgtct gggtaaatgc ttttaaatgc tctctcatct tgttcttccc   7440
cctcaccccc cactcttagg tatgtatgat gctaatcttg tccctaagta agttcttcc    7500
tgctcctttt gtatcttcct ttctttgtctt tcctcctacc ttttgtctct tggtgttttg   7560
```

```
gcactttttt tttttttttt ttgcccttttt gtacaaagat tagtttcaat gtagtctgta   7620
gcctccttttg taaaccaatt aaaaagtttt ttaataaaaa aaaaaaa                  7667
```

Figure 16C

```
Met Ser Asp Gln Asp His Ser Met Asp Glu Met Thr Ala Val Val Lys
1               5                   10                  15

Ile Glu Lys Gly Val Gly Gly Asn Gly Gly Asn Gly Asn Gly Gly
            20                  25                  30

Gly Ala Phe Ser Gln Ala Arg Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380
```

Figure 17A

```
Gln Lys Glu Gly Glu Gln Asn Gln Gln Thr Gln Gln Gln Ile Leu
385                 390                 395                 400

Ile Gln Pro Gln Leu Val Gln Gly Gly Gln Ala Leu Gln Ala Leu Gln
            405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
        435                 440                 445

Ile Ile Ile Arg Thr Pro Thr Val Gly Pro Asn Gly Gln Val Ser Trp
        450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
                485                 490                 495

Ser Ser Asn Thr Thr Leu Thr Pro Ile Ala Ser Ala Ser Ile Pro
            500                 505                 510

Ala Gly Thr Val Thr Val Asn Ala Ala Gln Leu Ser Ser Met Pro Gly
        515                 520                 525

Leu Gln Thr Ile Asn Leu Ser Ala Leu Gly Thr Ser Gly Ile Gln Val
        530                 535                 540

His Pro Ile Gln Gly Leu Pro Leu Ala Ile Ala Asn Ala Pro Gly Asp
545                 550                 555                 560

His Gly Ala Gln Leu Gly Leu His Gly Ala Gly Gly Asp Gly Ile His
                565                 570                 575

Asp Asp Thr Ala Gly Gly Glu Glu Gly Glu Asn Ser Pro Asp Ala Gln
            580                 585                 590

Pro Gln Ala Gly Arg Arg Thr Arg Arg Glu Ala Cys Thr Cys Pro Tyr
        595                 600                 605

Cys Lys Asp Ser Glu Gly Arg Gly Ser Gly Asp Pro Gly Lys Lys Lys
        610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
                645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
        675                 680                 685

Pro Glu Cys Pro Lys Arg Phe Met Arg Ser Asp His Leu Ser Lys His
        690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
                725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
```

Figure 17B

```
              755                 760                 765
   Val Met Gln Val Ala Asp Leu Gln Ser Ile Asn Ile Ser Gly Asn Gly
       770                 775                 780

Phe
   785
```

ATM-DEPENDENT PHOSPHORYLATION OF SP1 IS INVOLVED IN THE CELLULAR RESPONSE TO DNA DAMAGE AND ENHANCES CELLULAR SURVIVAL AFTER DNA DAMAGE

STATEMENT REGARDING FEDERALLY SPONSORED RESEARCH OR DEVELOPMENT

This invention was made, in part, using funds obtained from the U.S. Government (National Institutes of Health Grant No. CA71019 and CA91681), and the U.S. Government has certain rights in this invention.

BACKGROUND OF THE INVENTION

Sp1, one of the first gene-specific, metazoan transcription factors identified and cloned, is a ubiquitously expressed essential protein that regulates a variety of cellular and viral promoters (Dynan and Tjian, 1983, Cell 35:79-87; Jones and Tjian, 1985, Nature: 179-82; Kadonaga et al., 1987, Cell 51:1079-90; Marin et al., 1997, Cell 89:619-28; Saffer et al., 1991, Mol. Cell. Biol. 1:2189-99). Sp1 binds to DNA elements known as GC boxes via three $Cys_2His_2$ zinc finger domains, and interacts with the general transcription machinery through two glutamine-rich transactivation domains, designated A and B (FIG. 1) (Gidoni et al., 1984, Nature 312: 409-13; Gidoni et al., 1985, Science 230:511-7; Hoey et al., 1993, Cell 72:247-60; Kadonaga et al., 1987, Cell 51:1079-90; Tanese et al., 1996, Proc. Natl. Acad. Sci. U.S.A. 93:13611-6). The majority of TATA-less genes have multiple Sp1 sites in the proximal promoter region (Black et al., 1999, J. Biol. Chem. 274:1207-15), and more than half of expressed genes are TATA-less (Yang et al., 2000, FASEB J. 14:379-90). As such, Sp1 plays a global role in controlling gene expression.

Sp1 activity is significantly regulated through post-translational modifications, including phosphorylation, O-linked glycosylation, acetylation, and sumoylation (Jackson et al., 1990, Cell 63:155-65; Jackson and Tjian, 1988, Cell 55:125-33; Spengler and Brattain, 2006, J. Biol. Chem. 281:5567-74). The most studied modification is phosphorylation; Sp1 is phosphorylated by several kinases in vitro, including DNA-PK, casein kinase II, and cyclin A/cdk2, resulting in both positive and negative effects on transcription (Armstrong et al., 1997, J. Biol. Chem. 272:13489-95; Fojas de Borja et al., 2001, EMBO J. 20:5737-47; Jacksone et al., 1990, Cell 63:155-65 Ryu et al., 2003, J. Neuroscience 23:3597-606).

Several studies have also implicated Sp1 in the cellular response to DNA damage. In human cell lines exposed to ionizing radiation (IR), Sp1 DNA binding activity has been shown to increase in a transient and reversible manner (Meighan-Mantha et al., 1999, Mol. Cell. Biochem. 199:209-15; Yang et al., 2000, FASEB J. 14:379-90). Also, in cortical neurons, Sp1 DNA binding was shown to increase in response to oxidative stress, and Sp1 over-expression protected neurons from oxidative stress-induced cell death (Ryu et al., 2003, J. Neurosci. 23: 3597-606).

The human genome faces is continually threatened by DNA damage from reactive oxygen species (ROS) generated during aerobic respiration, cellular oxidase activity, and exposure to ionizing radiation (IR; Evans et al., 2004, Mutat. Res. 567:1-61). ROS-induced DNA damage includes small or bulky modifications to bases and sugars, inter- and intra-strand crosslinks, as well as single- and double-strand breaks (SSBs and DSBs, respectively) (Evans et al., 2004, Mutat. Res. 567:1-61; Roberfroid and Calderon, 1995, Free Radicals and Oxidation Phenomenon in Biological Systems. Marcel Dekker, Inc., New York). Molecular networks that rapidly sense and repair damage have evolved to maintain genomic stability and ensure cell survival.

Most threatening to genomic stability are DSBs, which activate the PI3 kinase-related kinases (PIKKs), including ATM (Ataxia-Telangiectasia Mutated), DNA-PK (DNA dependent protein kinase) and ATR (ATM and Rad3 related) (Abraham, 2004, DNA Repair 3:883-7). Cells deficient in PIKKs exhibit accumulated oxidative damage, radiation sensitivity, and impaired cell cycle checkpoint activation in response to DNA damage (Shiloh and Kastan, 2001, Adv. Cancer Res. 83:209-54). ATM protein, which is defective in the hereditary cancer-prone disorder Ataxia-Telangiectasia (A-T), is activated by DSBs and phosphorylates a variety of proteins involved in the DNA damage response leading to cell cycle checkpoint activation, DNA repair, altered gene expression patterns, and/or apoptosis (Shiloh, 2006, Trends Biochem. Sci. 31:402-10). Among the ATM substrates are several transcription factors, including p53 (Siliciano et al., Genes Dev. 11: 3471-81), BRCA-1 (Cortez et al., 1999, Science 286:1162-6), ATF2 (Bhoumik et al., 2001, Mol. Cell. 18:577-87), CREB (Shi et al., 2004, Proc. Natl. Acad. Sci. U.S.A. 101:5898-903), E2F1 (Lin et al., 2001, Genes Dev. 15:1833-44), and NF-κB regulators NEMO and IKK (Wu et al., 2006, Science, 311:1141-6). ATR, which is predominantly activated by bulky lesions and stalled replication forks, shares many substrates with ATM. The histone variant H2AX is phosphorylated by ATM, ATR and DNA-PK over a large region of chromatin surrounding a DSB (Rogakou et al., 1999, J. Cell. Biol. 146:905-16; Rogakou et al., 1998, J. Biol. Chem. 273: 5858-68).

Accumulated oxidative damage to genomic DNA is a recognized source of cancer; DSB are the single greatest threat to genomic stability whether caused by exposure to ROS generated during aerobic respiration, cellular oxidase activity, or exposure to ionizing radiation or chemotoxins. Methods of detecting DNA damage as a result of an individual's exposure to such agents are urgently needed, especially in the field of oncology. The present invention fulfills this need.

SUMMARY OF THE INVENTION

One embodiment of the invention comprises an antibody that specifically binds to Sp1 (SEQ ID NO.: 2) having a phosphate moiety at serine residue 101. In one aspect, the antibody is a polyclonal antibody, or fragment thereof. In another aspect, the antibody is a monoclonal antibody, or fragment thereof. In another aspect, the antibody comprises a detectable label. In still another aspect, the detectable label is selected from the group consisting of a radioactive, a fluorescent, a biological and an enzyme label.

Another embodiment of the invention comprises a method of detecting Sp1 (SEQ ID NO.: 2) having a phosphate moiety at serine residue 101 in a biological sample, the method comprising contacting a sample with an antibody, wherein the antibody specifically binds to said Sp1. In one aspect, the biological sample is a body sample. In another aspect, the antibody comprises a detectable label. In another aspect, the detectable label is selected from the group consisting of a radioactive, a fluorescent, a biological and an enzyme label.

Still another embodiment of the invention comprises a method of detecting DNA damage in a biological sample, the method comprising detecting Sp1 (SEQ ID NO.: 2) having a phosphate moiety at serine residue 101 in a sample with an antibody that specifically binds Sp1 having a phosphate moiety at serine residue 101, wherein when Sp1 having a phosphate at serine residue 101 is detected in the sample, DNA in the sample has been damaged. In one aspect, the biological sample is a body sample. In another aspect, the antibody comprises a detectable label. In still another aspect, the label is selected from the group consisting of a radioactive, a fluorescent, a biological and an enzyme label. In yet another aspect, the damage to DNA is a result of exposure to reactive oxygen species, cellular oxidase activity, ionizing radiation, a chemical cytotoxin, or any combination thereof. In still another aspect, the DNA damage comprises a modification to a base, a modification to a sugar, a single strand break or a double strand break.

Still another embodiment of the invention comprises a method of identifying an individual that has been exposed to a dose of ionizing radiation, a dose of chemotoxic agent, or any combination thereof sufficient to cause damage in the DNA of said individual, the method comprising detecting in a body sample obtained from the individual Sp1 (SEQ ID NO.: 2) having a phosphate moiety at serine residue 101, wherein when the Sp1 is detected in the sample, the individual has been exposed to a dose of ionizing radiation, a dose of chemotoxic agent, or any combination thereof sufficient to cause damage in the DNA of the individual. In one aspect, the method comprises an immunoassay for assessing the level of Sp1 having a phosphate moiety at serine residue 101 in the sample. In another aspect, the immunoassay is selected from the group consisting of Western blot, ELISA, immunoprecipitation, immunohistochemistry, immunofluorescence, radioimmunoassay, dot blotting, and FACS. In still another aspect, the method uses an antibody that specifically binds to Sp1 having a phosphate moiety at serine residue 101. In another aspect, the individual is a mammal. In still another aspect, the mammal is a human. In yet another aspect, the human is undergoing radiation therapy, chemotherapy or any combination thereof.

Another embodiment of the invention comprises a method of protecting a biological sample from DNA damage, the method comprising contacting the sample with an amount of Sp1 (SEQ ID NO.: 2) having a phosphate moiety at serine residue 101 effective to protect the sample from DNA damage. In one aspect, the biological sample is obtained from a mammal. In another aspect, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2A through FIG. 2E, is a series of images depicting time and dose-dependent modification of Sp1 in response to $H_2O_2$ and IR.

FIG. 2A is an image depicting an immunoblot of Sp1 prepared from NHDFs exposed to various concentrations of $H_2O_2$. FIG. 2B in an image depicting an immunoblot of Sp1 prepared from cells exposed to 200 μM $H_2O_2$ for one hour. FIG. 2C is an image depicting an immunoblot of Sp1 prepared from NHDFs exposed to 200 μM $H_2O_2$ for the indicated time periods and harvested directly in SDS sample buffer. FIG. 2D is an image depicting an immunoblot of Sp1 prepared from NHDF cells treated with the indicated dosage of ionizing radiation and harvested after 15 minutes. FIG. 2E is an image depicting an immunoblot of Sp1 prepared from NHDF cells treated with 20Gy ionizing radiation and harvested at the indicated time points. Immunoblots of Sp1 (top), γH2AX (middle), nucleolin (bottom) are shown.

FIG. 3A through FIG. 3C, is a series of images depicting ATM-dependence of $H_2O_2$-induced Sp1 phosphorylation. FIG. 3A is an image depicting an immunoblot of Sp1 (top), γH2AX (middle) and nucleolin (bottom) from NHDFs exposed to 200 μM $H_2O_2$ in the presence or absence of 20 or 100 μM wortmannin (Wort) or 10 μM KU55933 (KU; KuDos Pharmaceuticals, Cambridge, U.K.). FIG. 3B is an image depicting an immunoblot of Sp1 from M059K (DNA-PK+) and M059J (DNA-PK−) glioblastoma cells untreated or exposed to 600 μM $H_2O_2$ for one hour. FIG. 3C is an image depicting an immunoblot of GM03491 (AT wild-type fibroblasts) and GM02052 (AT mutant fibroblasts) exposed to the indicated amounts of $H_2O_2$ for 1 hour.

FIG. 4A through FIG. 4D, is a series of images depicting DNA-damage induced phosphorylation of Sp1 serine-101. FIG. 4A is an image depicting phosphoamino acid analysis of Sp1 from NHDFs exposed to 200 μM $H_2O_2$ for 1 hour in the presence of $^{32}P$-orthophosphate. FIG. 4B is an image depicting HeLa cells lysates separated by SDS-PAGE, following the cells' transfection with either wild-type Sp1 or mutant Sp1 wherein serine 101 is changed to either Ala (S101A) or Glu (S101E) by site-directed mutagenesis. FIG. 4C is an image depicting NHDFs treated for one hour with 200 μM $H_2O_2$ (+) or untreated (−), followed by lysis, SDS-PAGE and immunoblot with polyclonal antibody to Sp1 (pAb581) or γSp1$^{101}$. FIG. 4D is an image depicting NHDFs depleted of endogenous Sp1 by siRNA.

FIG. 5A through FIG. 5C, is a series of images depicting correlation of phosphorylation of Sp1 with increased chromatin association. FIG. 5A is an image depicting cytologic analysis of Sp1 from NHDFs exposed to 100 μM $H_2O_2$. FIG. 5B is an image depicting NHDFs that were exposed to 200 μM $H_2O_2$ (+) or left untreated (−) and treated with increasing amounts of salt to extract loosely associated proteins from chromatin. FIG. 5C is an image depicting an electrophoretic mobility shift assay (EMSA) in U2OS cells exposed to 200 μM $H_2O_2$ (+) or untreated (−) to determine Sp1 binding to its DNA consensus sequence in the presence of damage. The binding of Sp1 to its consensus sequence was shown to be specific through the inhibition of binding in the assay when Sp1 antibody was added (Ab) or when an excess of cold probe was added (cold probe) in the presence or absence of damage.

FIG. 6A through FIG. 6C, is a series of images depicting the co-localization of γSp1$^{101}$ with ionizing radiation induced foci (IRIF). FIG. 6A is an image depicting the phosphorylation of Sp1 in normal human diploid fibroblasts (NHDF) exposed to varying concentrations of ionizing radiation and harvested directly in SDS sample buffer 30 minutes after exposure. Immunoblots were performed with antibodies directed to Sp1 (top) γSp1$^{101}$, γH2AX, or α tubulin (bottom). FIG. 6B is a fluorescent photomicrograph depicting the co-localization of γH2AX and γSp1$^{101}$ by immunofluorescence in NHDF cells exposed to 0.5 Gy of IR and fixed 30 minutes after exposure. FIG. 6C is an image depicting the co-localization of γH2AX and γSp1[101] by confocal microscopy.

FIG. 7A is a graph depicting the results of clonogenic survival assays in NHDF following $H_2O_2$ exposure at the indicated concentration. FIG. 7B is a graph depicting the results of clonogenic survival assays in NHDF following IR. FIG. 7C is a graph depicting the results of clonogenic assays in U2OS following $H_2O_2$. FIG. 7D is a graph depicting the results of clonogenic survival assays in U2OS following IR. Inset, shows Sp1 (top) and nucleolin (bottom) levels 72 hours after transfection with Sp1 or non-targeting (NT) siRNA.

FIG. 8A and FIG. 8B, is a series of images depicting the rescue of increased sensitivity in cells depleted of Sp1 by wild-type Sp1 but not the phospho-mutant Sp1 101A. FIG. 8A is a graph depicting the results of clonogenic survival assays in U2OS cells depleted of Sp1 using siRNA or non-targeting control (NT) siRNA as a control. Sp1WT or Sp1S101A was then reintroduced into cells. Cells were then exposed to the indicated amount of $H_2O_2$ for one hour. After 11 days, discrete colonies were stained with crystal violet and counted in a blinded manner. Data are expressed relative to the # of colonies in the non-treated cells of samples receiving the same DNAs. FIG. 8B is an image depicting expression of exogenous Sp1 in U2OS cells exposed to the indicated concentrations of $H_2O_2$ for one hour and harvested directly in SDS sample buffer. Immunoblots were performed with antibody specific to HA.11 or γSp1[101]. Inset, shows Sp1 (top) and nucleolin (bottom) levels 72 hours after transfection with Sp1 or non-targeting control (NT) siRNA.

FIG. 9A through FIG. 9D, is a series of images depicting formation of increased numbers of IR-induced γH2AX foci in NHDFs or U2OS cells depleted of Sp1 by RNAi. FIG. 9A is an image depicting representative NHDF cells from each group shown with an immunoblot to the right showing specific knockdown of Sp1. FIG. 9B is a graph depicting quantitative analysis of foci of γH2AX counted in at least 30 NHDF cells. Each data point represents the average # of foci per cell ±SEM. FIG. 9C is an image depicting representative U2OS cells from each group shown with an immunoblot to the right showing specific knockdown of Sp1. FIG. 9D is a graph depicting quantitative analysis of foci of γH2AX counted in at least 30 cells. Each data point represents the average # of foci per cell ±SEM. The * represents significant differences of $p<0.01$ at 10 minutes and $p=0.024$ at 4 hrs in FIG. 9B and $p<0.001$ at all time points in FIG. 9D.

FIG. 10A and FIG. 10B, is a series of images depicting increase in apoptosis in U2OS cells in the absence of Sp1. FIG. 10A is an image that depicts an increase in TUNEL staining in cells depleted of Sp1 by siRNA after exposure to 400 μM $H_2O_2$ for four hours. FIG. 10B is a graph depicting quantitative analysis of TUNEL positive cells counted in at least 300 cells. The * represents a significant difference of $p<0.001$.

FIG. 12A is an image that depicts a chromatin immunoprecipitation analysis of U2OS cells that were infected with a specific restriction enzyme (HA-ER-I-PpoI) which induces double strand breaks at known sites. Twenty-four hours after infection, cells were untreated (−) or treated (+) with 4 μM 4-OHT (Tamoxifen®) to increase the transport of the HA-ER-I-PpoI into the nucleus. Sixteen hours after induction with 4-OHT, U2OS cells were fixed in formaldehyde and subjected to ChIP analysis using oligonucleotide primers specific for the 28S rDNA I-PpoI target site (489 bp 3' to the I-PpoI cut site). GAPDH has no I-PpoI sites and therefore is used as a genomic DNA control. FIG. 12B depicts U2OS cells that were induced with 4-OHT after HA-ER-I-PpoI infection. Sixteen hours after induction with 4-OHT, U2OS cells were fixed in formaldehyde and subjected to ChIP analysis using oligonucleotide primers specific for the I-PpoI target site on chromosome 1 (280 bp 5' to the I-PpoI cut site). GAPDH has no I-PpoI sites and therefore is used as a genomic DNA control. FIG. 12C is an image that depicts U2OS infected with HA-ER-I-PpoI and induced with 4-OHT. Sixteen hours after treatment with 4-OHT, cells were harvested in 1×SDS sample buffer and analyzed by immunoblot for HA (top), Sp1, γSp1[101], NBS1, γH2AX, and α-tubulin (bottom).

FIG. 13A through FIG. 13D, is a series of images that depict the dose- and time-dependent phosphorylation of Sp1 in response to ultra-violet light. FIG. 13A is an image depicting an immunoblot of Sp1 prepared from NHDFs exposed to the indicated dose of UV. FIG. 13B in an image depicting an immunoblot of Sp1 prepared from cells exposed to 30 J/m2 UV for four hours. FIG. 13C is an image depicting an immunoblot of Sp1 prepared from U2OS cells treated with the indicated dosage of UV and harvested after four hours. FIG. 13D is an image depicting an immunoblot of Sp1 prepared from U2OS cells treated with 30 J/m2 ultra-violet light and harvested at the indicated time points. Immunoblots of Sp1 (top), γSp1[101], γH2AX, and α-tubulin (bottom) are shown.

FIG. 14A is an image depicting U2OS cells in either the absence or presence of 10 μM ATM inhibitor KU55933 (KU) for one hour prior to being exposed to 200 μM $H_2O_2$ for an additional one hour or 30 J/m$^2$ UV for four hours or untreated (−). Cells were harvested in 1×SDS sample buffer and immunoblots were performed with Sp1 (top), γSp1[101], γH2AX, and nucleolin (bottom) as indicated. FIG. 14B is an image depicting U2OS cells exposed to 0.5 J/m$^2$ of UV and processed for indirect immunofluorescence four hours later using antibodies to γSp1[101] or phospho-ATMs1981 in either the absence or presence of 10 μM ATM inhibitor KU55933.

FIG. 15A through FIG. 15C, is a series of images that depicts the sensitivity of the phosphorylation of Sp1 in response to damage as compared to the known marker of DNA double strand breaks, H2AX, in response to a variety of chemotherapeutic agents. FIG. 15A depicts an image of U2OS cells untreated (No Tx) or exposed to low and high dose chemotherapeutic agents (+ for low or ++ for high). The concentrations were 5 and 15 μM doxorubicin (Doxo), 50 and 100 μg/ml Bleomycin (Bleo), 5 and 10 μM Etopsoide (Etop), 5 and 20 μM Camptothecin (Camp), and 200 μM $H_2O_2$ for 1 hour. FIG. 15 B is an image that depicts the phosphorylation of Sp1 in response to varying concentration of hydroxyurea (HU). U2OS cells were harvested 24 hours after treatment with the drug. FIG. 15C is an image that depicts phosphorylation of Sp1 in response to varying concentration of methotrexate (MTX) 24 hours after exposure. Immunoblots were performed for Sp1 (top), $\gamma Sp1^{101}$, $\gamma$H2AX, and nucleolin (bottom) as indicated. There was no visualization of H2AX phosphorylation in cells exposed to methotrexate.

FIG. 16, comprising FIGS. 16A-16C, is an image depicting the nucleic acid sequence encoding Sp1 (SEQ ID NO: 1).

FIG. 17, comprising FIGS. 17A-17C, is an image depicting the protein sequence of Sp1 (SEQ ID NO: 2).

DETAILED DESCRIPTION OF THE INVENTION

Figure 1:
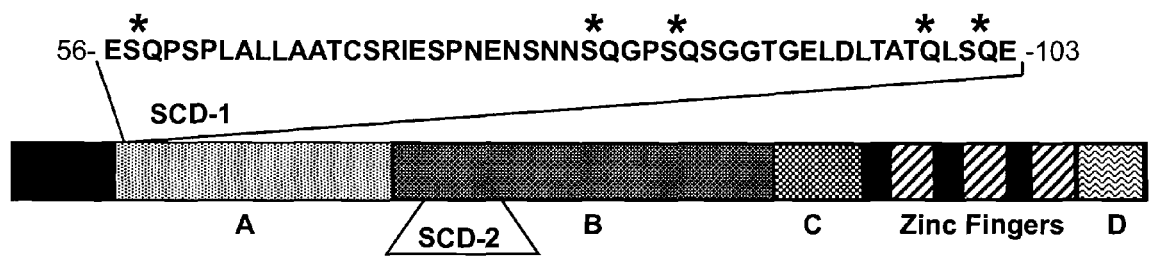
FIG. 1 is an image depicting a schematic diagram of Sp1. Sp1 has been divided into 5 domains based upon amino acid composition and functional analysis of deletion mutants (Courey and Tjian, 1988, Cell 55:887-98). A and B are transactivation domains (ca. amino acids 85-220 and 261-495, respectively) that have Ser/Thr-rich and glutamine rich segments. S/TQ cluster domains (SCDs) within each of these are shown. The amino acid sequence of the SCD in the A domain is shown above. The C domain (ca. aa 496-610) is a highly charged transactivation domain; the DNA binding domain (aa 615-708) contains three zinc finger motifs; and the D domain (ca. aa 708-785) mediates Sp1 multimerization and superactivation (Pascal and Tjian, 1991, Genes Dev. 5:1646-56).

It has been discovered in the present invention that the phosphorylation of serine residue 101 of the Sp1 protein (SEQ ID NO.: 2 is correlated with enhanced cellular viability in response to DNA damage. The present invention provides materials and methods for identifying cells with DNA damage as well as individuals exposed to ionizing radiation or chemotoxins in doses sufficient to cause DNA damage.

Definitions:

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used in this specification and the appended claims, the singular forms "a", "an", and "the" include plural referents unless the content clearly dictates otherwise. Thus, for example, reference to "a protein" includes a combination of two or more proteins, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks the biological activity of the antigen.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "DNA" as used herein is defined as deoxyribonucleic acid.

A "putative at-risk individual" is a mammal, preferably a human, who is thought to be at risk of DNA damage. An individual's DNA damage may be age-related, a result of an individual's exposure to ionizing radiation or chemotoxins, including but not limited to agents used in chemotherapy for the treatment of various cancers, or any combination thereof.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "phosphoserine$^{101}$ Sp1" as used herein refers to Sp1 (SEQ ID NO.: 2) having a phosphate moiety at serine residue 101 of SEQ ID NO.: 2.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By the term "specifically binds," as used herein, is meant a molecule, such as an antibody, which recognizes and binds to a specific molecule or feature, but does not substantially recognize or bind other molecules or features in a sample.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Description:

The compositions and methods of the present invention are intended for detecting DNA damage in a biological sample obtained from an individual, preferably a human. Age-related DNA damage may be accrued over time as a result of chronic exposure to reactive oxygen species generated during aerobic respiration and cellular oxidase activity. DNA damage also results from exposure to sufficiently high doses of ionizing radiation (IR), chemotoxic agents, or a combination thereof. DNA damage is the biggest threat to genomic stability and a recognized cause of cancer. Detection of DNA damage in a cell is useful for identifying an individual at risk of developing clinical sequelae to radiation or chemotoxin exposure as well as monitoring therapeutic effects during clinical trials and other treatment, such as radiation or chemotherapy. Thus, the therapeutic effectiveness of an agent, such as a radionucleide for radiation therapy or a cytotoxic agent for chemotherapy designed to cause DNA damage in a cell, can be monitored using phosphoserine$^{101}$ Sp1 as an end-point target.

In experimental examples set forth herein for the first time, the present invention discloses that phosphorylation of Sp1 (SEQ ID NO: 2; FIG. 17) at serine 101 is an essential component of a cell's physiological response to DNA damage and is correlated with increased cellular viability in response to DNA damage. Accordingly, the present invention provides an antibody that specifically binds to Sp1 only when Sp1 has a phosphate moiety at serine 101.

The present invention further provides methods for determining whether an individual has been exposed to ionizing radiation (IR) and chemotoxic agents in doses sufficient to destabilize the genome and cause DNA damage therein by measuring phosphoserine$^{101}$ Sp1 levels in biological samples obtained from the individual.

In another embodiment of the invention, methods are provided to protect or stabilize DNA from damage following an individual's exposure to IR, chemotoxins or any agent that is capable of inducing DNA damage by increasing expression of phosphoserine$^{101}$ Sp1.

Biological Sample

The composition of the present invention comprises an antibody that specifically binds to Sp1 in a biological sample when a phosphate moiety is present at serine 101. It will be appreciated by one skilled in the art that a biological sample may comprise any primary isolated or cultured cell, tissue, organ or body sample. A body sample is any sample comprising a cell, a tissue, or a bodily fluid in which expression of a protein, a polynucleotide, and/or a biomolecule can be detected. Examples of such body samples include but are not limited to blood, lymph, bone marrow, biopsies, and smears. Samples that are liquid in nature are referred to herein as "bodily fluids." Body samples may be obtained from an individual by a variety of techniques including, for example, by scraping or swabbing an area or by using a needle to aspirate bodily fluids. Methods for collecting various body samples are well known in the art. One of ordinary skill in the art will be familiar with the histological techniques and procedures used in the preparation of a biological sample for subsequent detection of a protein of interest, preferably phosphoserine$^{101}$ Sp1.

Peptides

The antibody of the present invention is used to detect a phosphorylated protein, preferably phosphoserine$^{101}$ Sp1. The peptide sequence Acetyl-DLTATQL[pS]QGANGK-amide (SEQ ID NO.: 14) was used as an antigen to inoculate a rabbit, where [pS] represents a phosphorylated serine residue. A high affinity polyclonal antibody that specifically recognized phosphoserine$^{101}$ Sp1 was obtained and this antibody is designated γSp1$^{101}$. It will be appreciated by one skilled in the art that any variant on this antigenic peptide (SEQ ID NO.: 14) could be used as an antigen, to generate an antibody useful in the present invention provided that the antibody specifically binds Sp1 including a phosphate group at position 101. For example, the full length phosphoserine$^{101}$ Sp1 protein can be used as an antigen, or any fragments thereof, provided they include a phosphorylated serine that corresponds to position 101 of the full length protein and provided that any antibody generated using this antigen specifically binds Sp1 including a phosphate group at position 101.

Phosphoserine$^{101}$ Sp1, or any fragment or variant thereof, can be comprised of chemically synthesized or recombinantly produced peptides or proteins (e.g. in bacteria, yeast, insect or mammalian expression systems), enzymatically phosphorylated peptides or proteins, or naturally purified peptides or proteins. The length of the peptide should be such that an immune response is generated when the antigen is coupled with a carrier and injected into a host animal. The length of the antigenic peptide can range from about 6 amino acids and extends to any length up to full-length phosphoserine$^{101}$ Sp1 protein.

The present invention further provides polypeptides encoded by SEQ ID NO. 1 (FIG. 16) and variants thereof, which can be used an antigenic peptides. Polypeptides useful by the invention include those encoded by the disclosed nucleic acids, as well as nucleic acids that, by virtue of the degeneracy of the genetic code, are not identical in sequence to the disclosed nucleic acids, and variants thereof.

In general, the term "polypeptide" as used herein refers to both the full length polypeptide encoded by the recited nucleic acid, the polypeptide encoded by the gene represented by the recited nucleic acid, as well as portions or fragments thereof. "Polypeptides" also includes variants of the naturally occurring proteins, where such variants are homologous or substantially similar to the naturally occurring protein, and can be of an origin of the same or different species as the naturally occurring protein (e.g., human, murine, or some other species that naturally expresses the recited polypeptide, usually a mammalian species). In general, variant polypeptides have a sequence that has at least about 80%, usually at least about 90%, and more usually at least about 98% sequence identity with a differentially expressed polypeptide described herein, as measured by BLAST 2.0 using the parameters described above. The variant polypeptides can be naturally or non-naturally glycosylated, i.e., the polypeptide has a glycosylation pattern that differs from the glycosylation pattern found in the corresponding naturally occurring protein. In addition the variant polypeptides can be naturally or non-naturally phosphorylated.

In general, the polypeptides of the subject invention are provided in a non-naturally occurring environment, e.g. are isolated. In certain embodiments, the subject protein is present in a composition that is enriched for the protein as compared to a control. As such, purified polypeptides are provided, where by purified is meant that the protein is present in a composition that is substantially free of non-differentially expressed polypeptides, where by substantially free is meant that less than 90%, usually less than 60% and more usually less than 50% of the composition is made up of non phosphoserine$^{101}$ Sp1 polypeptides.

Variant polypeptides can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the protein (e.g., a functional domain and/or, where the polypeptide is a member of a protein family, a region associated with a consensus sequence).

Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by SEQ ID NO: 1, or a homolog thereof. Polypeptide regions of particular interest will include the serine at residue 101 of SEQ ID NO.: 2.

Phosphoserine$^{101}$ Sp1 Detection

In one embodiment, the method of the invention comprises collecting a biological sample, contacting the sample with at least one antibody specific for a protein of interest, and detecting antibody binding thereto.

Methods for detecting phosphoserine$^{101}$ Sp1 comprise any method that determines the quantity or the presence of phosphoserine$^{101}$ Sp1 at the protein level. Such methods are well known in the art and include but are not limited to western blots, ELISA, immunoprecipitation, immunofluorescence, flow cytometry, and immunocytochemistry.

The invention should not be limited to any one method of protein detection method recited herein, but rather should encompass all known or heretofore unknown methods of detection as are, or become, known in the art.

In one embodiment, antibodies specific for phosphoserine$^{101}$ Sp1 are used to detect protein in a biological sample. The method comprises obtaining a biological sample, contacting the biological sample with at least one antibody directed to phosphoserine$^{101}$ Sp1 in the biological sample, then detecting the antibody bound to phosphoserine$^{101}$ Sp1 in the biological sample. One of skill in the art will recognize that the immunocytochemistry method described herein below is performed manually or in an automated fashion.

When the antibody used in the methods of the invention is a polyclonal antibody (IgG), the antibody is generated by inoculating a suitable animal with a biomarker protein, peptide or a fragment thereof. Antibodies produced in the inoculated animal which specifically bind the biomarker protein are then isolated from fluid obtained from the animal. Antibodies may be generated in this manner in several non-human mammals such as, but not limited to goat, sheep, horse, rabbit, and donkey. Methods for generating polyclonal antibodies are well known in the art and are described, for example in Harlow, et al. (1988, In: Antibodies, A Laboratory Manual, Cold Spring Harbor, N.Y.). These methods are not repeated herein as they are commonly used in the art of antibody technology.

When the antibody used in the methods of the invention is a monoclonal antibody, the antibody is generated using any well known monoclonal antibody preparation procedures such as those described, for example, in Harlow et al., (1988, In: Antibodies, A Laboratory Manual, Cold Spring Harbor, N.Y.), and in Tuszynski et al. (1988, Blood, 72:109-115). Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of biomarker may be prepared using the techniques described in Harlow, et al. (1988, In: Antibodies, A Laboratory Manual, Cold Spring Harbor, N.Y.).

Samples may need to be modified in order to render phosphoserine[101] Sp1 antigens accessible to antibody binding. In a particular aspect of the immunocytochemistry methods, slides are transferred to a pretreatment buffer, for example phosphate buffered saline containing Triton-X. Incubating the sample in the pretreatment buffer rapidly disrupts the lipid bilayer of the cells and renders the antigens (i.e., biomarker proteins) more accessible for antibody binding. The pretreatment buffer may comprise a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffers of the invention are used in methods for making antigens more accessible for antibody binding in an immunoassay, such as, for example, an immunocytochemistry method or an immunohistochemistry method.

Any method for making antigens more accessible for antibody binding may be used in the practice of the invention, including antigen retrieval methods known in the art. See, for example, Bibbo, 2002, Acta. Cytol. 46:25 29; Saqi, 2003, Diagn. Cytopathol. 27:365 370; Bibbo, 2003, Anal. Quant. Cytol. Histol. 25:8 11. In some embodiments, antigen retrieval comprises storing the slides in 95% ethanol for at least 24 hours, immersing the slides one time in Target Retrieval Solution pH 6.0 (DAKO S1699)/dH$_2$O bath preheated to 95° C., and placing the slides in a steamer for 25 minutes.

Following pretreatment or antigen retrieval to increase antigen accessibility, samples are blocked using an appropriate blocking agent, e.g., a peroxidase blocking reagent such as hydrogen peroxide. In some embodiments, the samples are blocked using a protein blocking reagent to prevent nonspecific binding of the antibody. The protein blocking reagent may comprise, for example, bovine serum albumin, purified casein, serum, or solution of milk proteins. An antibody directed to phosphoserine[101] Sp1 is then incubated with the sample.

As noted elsewhere herein, one of skill in the art will appreciate that it may be of interest to detect phosphoserine[101] Sp1 in a biological sample in addition to another protein of interest in the same sample. Therefore, in particular embodiments, at least two antibodies, one that specifically binds phosphoserine[101] Sp1 and at least one other antibody that binds another distinct protein of interest, are used. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled.

Techniques for detecting antibody binding are well known in the art. Antibody binding to phosphoserine[101] Sp1 may be detected through the use of chemical reagents that generate a detectable signal that corresponds to the level of antibody binding and, accordingly, to the level of phosphoserine[101] Sp1 expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of phosphoserine[101] Sp1. Enzymes of particular interest include horseradish peroxidase (HRP) and alkaline phosphatase (AP). Commercial antibody detection systems, such as, for example the Dako Envision+system (Dako North America, Inc., Carpinteria, Calif.) and Mach 3 system (Biocare Medical, Walnut Creek, Calif.), may be used to practice the present invention.

In one particular immunocytochemistry method of the invention, antibody binding to a phosphoserine[101] Sp1 is detected using an HRP-labeled polymer that is conjugated to a secondary antibody. Antibody binding can also be detected using a mouse probe reagent which binds to mouse monoclonal antibodies, and a polymer conjugated to HRP, which binds to the mouse probe reagent. Slides are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, slides are reviewed microscopically by a cytotechnologist and/or a pathologist to assess cell staining (i.e., biomarker overexpression). Alternatively, samples may be reviewed via automated microscopy or by personnel with the assistance of computer software that facilitates the identification of positive staining cells.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^3$H.

In regard to detection of antibody staining in the immunocytochemistry methods of the invention, there also exist in the art video-microscopy and software methods for the quantitative determination of an amount of multiple molecular species (e.g., biomarker proteins) in a biological sample, wherein each molecular species present is indicated by a representative dye marker having a specific color. Such methods are also known in the art as colorimetric analysis methods. In these methods, video-microscopy is used to provide an image of the biological sample after it has been stained to visually indicate the presence of a particular protein of interest. Some of these methods, such as those disclosed in U.S. Pat. Nos. 7,065,236 and 7,133,547 to Marcelpoil, incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the proteins of interest. Methods for making antibodies and for selecting appropriate antibodies are known in the art. See, for example, Celis, J. E. ed., 1998, Cell Biology & Laboratory Handbook, 3rd edition (Academic Press, New York), which is herein incorporated in its entirety by reference. The antibodies of the invention may be selected on the basis of desirable staining of cytological, rather than histological, samples. That is, in particular embodiments the antibodies are selected with the end sample type (i.e., cytology preparations) in mind and for binding specificity.

One of skill in the art will recognize that optimization of antibody titer and detection chemistry is needed to maximize the signal to noise ratio for a particular antibody. Antibody concentrations that maximize specific binding to phosphoserine$^{101}$ Sp1 and minimize non-specific binding (or "background") will be determined in reference to the type of biological sample being tested. In particular embodiments, appropriate antibody titers for use cytology preparations are determined by initially testing various antibody dilutions on formalin-fixed paraffin-embedded normal tissue samples. Optimal antibody concentrations and detection chemistry conditions are first determined for formalin-fixed paraffin-embedded tissue samples. The design of assays to optimize antibody titer and detection conditions is standard and well within the routine capabilities of those of ordinary skill in the art. After the optimal conditions for fixed tissue samples are determined, each antibody is then used in cytology preparations under the same conditions. Some antibodies require additional optimization to reduce background staining and/or to increase specificity and sensitivity of staining in the cytology samples.

Furthermore, one of skill in the art will recognize that the concentration of a particular antibody used to practice the methods of the invention will vary depending on such factors as time for binding, level of specificity of the antibody for the biomarker protein, and method of body sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

As noted, it is contemplated that the antibody of the invention (e.g. γSp1$^{101}$) will find utility in immunohistochemistry and in ELISA assays. One evident utility of the phosphoserine$^{101}$ Sp1 antigens and corresponding antibodies is in immunoassays for the detection of phosphoserine$^{101}$ Sp1 protein, as needed in diagnosis and prognostic monitoring.

Immunoassays

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the biomarker proteins of the invention are immobilized onto a selected surface exhibiting protein affinity, such as a well in a polystyrene microtiter plate. Then, a test composition suspected of containing the phosphoserine$^{101}$ Sp1 antigen, such as a clinical sample, is added to the wells. After binding and washing to remove non-specifically bound immunocomplexes, the bound antibody may be detected. Detection is generally achieved by the addition of a second antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the phosphoserine$^{101}$ Sp1 antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the biomarker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as, but not limited to, BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immune complex can be detected with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

DNA Damage

The methods of the present invention are intended for detecting DNA damage in a cell, tissue or other body sample obtained from an individual, preferably a human. Damage to DNA may have a genetic- or age-related basis or may result from exposure to agents including those which generate DNA adducts by alkylation (e.g., methylmethane sulfonate (MMS), ethylmethane sulfonate (EMS), N-methyl-N-nitro-N-nitrosoguanine (MNNG), dimethylnitrosamine (DMN), dimethyl sulfate), and form intra- and inter-strand crosslinks (e.g., mitomycin C, bleomycin, etoposide, psoralens). Furthermore, exposure to base analogs, such as bromouracil and aminopurine; nucleotide synthesis inhibitors, such as hydroxyurea or methotrexate; nitrous acid; large molecules which bind to bases in DNA and cause them to be noncoding, i.e., "bulky" lesions; chemicals causing DNA strand breaks (e.g., peroxides); reactive oxygen species (ROS) generated during aerobic respiration, cellular oxidase activity; and radiation such as ultraviolet and ionizing radiation (e.g., X- and gamma-rays) also result in DNA damage.

Detection of DNA damage in a cell as determined by the phosphorylation state of Sp1 is also useful for monitoring therapeutic effects during clinical trials and other treatment, such as radiation therapy. Thus, the therapeutic effectiveness of an agent, such as a radionucleide for radiation therapy or a cytotoxic agent for chemotherapy designed to cause DNA damage in a cell, can be monitored using phosphoserine$^{101}$ Sp1 as an end-point target.

Phosphoserine$^{101}$ Sp1 Expression

The invention contemplates a method of producing soluble phosphoserine$^{101}$ Sp1 to be used either prophylactically in anticipation of exposure to of an individual IR, chemotoxins or any DNA-damaging agent, or to be administered to the individual following exposure to same. In addition, the invention contemplates administering soluble phosphoserine$^{101}$ Sp1 to an individual wherein DNA damage occurs as a product of repeated exposure to reactive oxygen species (ROS) generated during aerobic respiration and/or cellular oxidase activity.

It will be appreciated by those skilled in the art that various modifications of the Sp1 having the sequence of SEQ ID NO. 2 or functionally equivalent fragments of SEQ ID NO. 2 can be made without departing from the essential nature of the invention. Accordingly, it is intended that polypeptides which have the amino acid sequence of SEQ ID NO. 2 but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids within the following groups: (1) M, I, L, V; (2) F, Y, W; (3) K, R, H; (4) A, G; (5) S, T; (6) Q, N; and, (7) E, D. Fusion proteins, in which a peptide of the invention is coupled to a solid support (such as a polymeric bead), a carrier molecule (such as keyhole limpet hemocyanin), or a reporter group (such as radiolabel or other tag), or a membrane anchoring group (such a myristoylation peptide) also are embraced within the invention.

Preferred Sp1s further include Sp1s that have a post-translational modification. Such modifications include, but are not limited to, phosphorylation, acetylation, glycosylation, sumoylation, and methylation.

Nucleic acids encoding Sp1 may be incorporated into a recombinant expression vector in a form suitable for expression of the proteins in a host cell. A suitable form for expression provides that the recombinant expression vector includes one or more regulatory sequences operatively-linked to the nucleic acids encoding Sp1 in a manner that allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel, Gene Expression Technology Methods in Enzymology 185, Academic Press, San Diego, Calif. (1990). It should be understood that the design of the expression vector may depend on such factors as the choice of the host cell to be transfected and/or the level of expression required.

Soluble Sp1 of the invention may be expressed not only directly, but also as a fusion protein with a heterologous polypeptide, i.e. a signal sequence for secretion and/or other polypeptide which will aid in the purification of Sp1. These heterologous polypeptides can be phosphorylated using a kinase.

In general, a signal sequence may be a component of the vector and should be one that is recognized and processed (i.e., cleaved by a signal peptidase) by the host cell. For production in a prokaryote, a prokaryotic signal sequence from, for example, alkaline phosphatase, penicillinase, 1pp, or heat-stable enterotoxin II leaders may be used. For yeast secretion, one may use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example the herpes simplex glycoprotein D signal may be used.

Other useful heterologous polypeptides which may be fused to Sp1 include those which increase expression or solubility of the fusion protein or aid in the purification of the fusion protein by acting as a ligand in affinity purification. Typical fusion expression vectors include those exemplified herein as well as pGEX (Amersham Pharmacia Biotech, Uppsala, Sweden; Smith, and Johnson (1988) Gene 67:31 40), pMAL (New England Biolabs, Beverly, Mass.) and pRIT5 (Pharmacia, Piscataway, N.J.) which fuse GST, maltose E binding protein, or protein A, respectively, to the target recombinant protein.

Eukaryotic microbes such as yeast may be transformed with suitable vectors containing nucleic acids encoding Sp1. *Saccharomyces cerevisiae* is the most commonly studied lower eukaryotic host microorganism, although a number of other species are commonly available. Yeast vectors may contain an origin of replication from the 2 micron yeast plasmid or an autonomously replicating sequence (ARS), a promoter, nucleic acid sequences encoding Sp1, sequences for polyadenylation and transcription termination, and nucleic acid sequences encoding a selectable marker. Exemplary plasmids include YRp7 (Stinchcomb, et al. (1979) Nature 282:39; Kingsman, et al. (1979) Gene 7:141; Tschemper, et al. (1980) Gene 10:157), pYepSec1 (Baldari, et al. (1987) EMBO J. 6:229 234), pMFa (Kurjan and Herskowitz (1982) Cell 30:933 943), pJRY88 (Schultz, et al. (1987) Gene 54:113 123), and pYES2 (INVITROGEN.TM. Corporation, San Diego, Calif.). These plasmids contain genes such as trp1, which provides a selectable marker for a mutant strain of yeast lacking the ability to grow in the presence of tryptophan, for example ATCC No. 44076 or PEP4-1 (Jones (1977) Genetics 85:12). The presence of the trp1 lesion in the yeast host cell genome then provides an effective environment for detecting transformation by growth in the absence of tryptophan.

Suitable sequences for promoting Sp1 expression in yeast vectors include the promoters for metallothionein, 3-phosphoglycerate kinase (Hitzeman, et al. (1980) J. Biol. Chem. 255:2073) or other glycolytic enzymes (Hess, et al. (1968) J. Adv. Enzyme Reg. 7:149; Holland, et al. (1978) Biochemistry 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further disclosed in EP 73,657.

In mammalian cells the recombinant expression vector may be a plasmid. Alternatively, a recombinant expression vector may be a virus, or a portion thereof, which allows for expression of a nucleic acid introduced into the viral nucleic acid. For example, replication-defective retroviruses, adenoviruses and adeno-associated viruses may be used. Protocols for producing recombinant retroviruses and for infecting cells in vitro or in vivo with such viruses may be found in Current Protocols in Molecular Biology, Ausubel, F. M. et al. (eds.) Greene Publishing Associates, (1989), Sections 9.10 9.14 and other standard laboratory manuals. Examples of suitable retroviruses include, but are not limited to, pLJ, pZIP, pWE, pBABE, and pEM which are well-known to those skilled in the art. Examples of suitable packaging virus lines include, but are not limited to 293T cells, ψCrip, ψCre, ψ2 and ψAm. The genome of adenovirus may be manipulated such that it encodes and expresses Sp1 but is inactivated in terms of its ability to replicate in a normal lytic viral life cycle (Berkner, et al. (1988) BioTechniques 6:616; Rosenfeld, et al. (1991) Science 252:431 434; Rosenfeld, et al. (1992) Cell 68:143 155). Suitable adenoviral vectors derived from the adenovirus strain Ad type 5 dl324 or other strains of adenovirus (e.g., Ad2, Ad3, Ad7 etc.) are well-known to those skilled in the art. Alternatively, an adeno-associated virus vector such as that taught by Tratschin, et al. ((1985) Mol. Cell. Biol. 5:3251 3260) may be used to express Sp1.

In mammalian expression systems, the regulatory sequences are often provided by the viral genome. Commonly used promoters are derived from polyoma, Adenovirus 2, cytomegalovirus and Simian Virus 40. For example, the human cytomegalovirus IE promoter (Boshart, et al. (1985) Cell 41:521 530), HSV-TK promoter (McKnight, et al. (1984) Cell 37:253 262) and β-actin promoter (Ng, et al. (1985) Mol. Cell. Biol. 5:2720 2732) may be useful in the expression of Sp1 in mammalian cells. Alternatively, the regulatory sequences of the recombinant expression vector may direct expression of Sp1 preferentially in a particular cell type, i.e., tissue-specific regulatory elements can be used. Examples of tissue-specific promoters which may be used include, but are not limited to, the albumin promoter (liver-specific; Pinkert, et al. (1987) Genes Dev. 1:268 277), lymphoid-specific promoters (Calame and Eaton (1988) Adv. Immunol. 43:235 275), promoters of T cell receptors (Winoto and Baltimore (1989) EMBO J. 8:729 733) and immunoglobulins (Banerji, et al. (1983) Cell 33:729 740; Queen and Baltimore (1983) Cell 33:741 748), neuron-specific promoters (e.g., the neurofilament promoter; Byrne and Ruddle (1989) Proc. Natl. Acad. Sci. USA 86:5473 5477), pancreas-specific promoters (Edlund, et al. (1985) Science 230:912 916), and mammary gland-specific promoters (e.g., milk whey promoter; U.S. Pat. No. 4,873,316; EP 264,166). Developmentally-regulated promoters are also encompassed, for example the murine hox promoters (Kessel and Gruss (1990) Science 249:374 379) and the .alpha.-fetoprotein promoter (Camper and Tilghman (1989) Genes Dev. 3:537 546).

When the host cell is from an insect (e.g., *Spodoptera frugiperda* cells), expression vectors such as the baculovirus expression vector (e.g., vectors derived from *Autographa californica* MNPV, *Trichoplusia ni* MNPV, *Rachiplusia ou* MNPV, or *Galleria ou* MNPV, as described in U.S. Pat. Nos. 4,745,051 and 4,879,236) may be employed to express Sp1. In general, a baculovirus expression vector comprises a baculovirus genome containing nucleic acid sequences encoding Sp1 inserted into the polyhedrin gene at a position ranging from the polyhedrin transcriptional start signal to the ATG start site and under the transcriptional control of a baculovirus polyhedrin promoter.

*Escherichia coli* is the most common prokaryotic expression system. Exemplary *E. coli* strains include W3110 (ATCC 27325), *E. coli* B, *E. coli* X1776 (ATCC 31537), and *E. coli* 294 (ATCC 31446). *E. coli* is typically transformed using pBR322 (Bolivar, et al. (1977) Gene 2:95) and derivatives thereof.

Promoters most commonly used in recombinant prokaryotic expression vectors include the beta-lactamase (penicillinase) and lactose promoter systems (Chang, et al. (1978) Nature 275:615; Goeddel, et al. (1979) Nature 281:544), a tryptophan (trp) promoter system (Goeddel, et al. (1980) Nucl. Acids Res. 8:4057; EP 36,776) the tac promoter (De Boer, et al. (1983) Proc. Natl. Acad. Sci. USA 80:21) and pL of bacteriophage 1. These promoters and Shine-Dalgarno sequence may be used for efficient expression of Sp1 in prokaryotes.

Sp1 is expressed in a cell by introducing nucleic acid sequences encoding Sp1 into a host cell, wherein the nucleic acids are in a form suitable for expression of Sp1 in the host cell. Alternatively, nucleic acid sequences encoding Sp1 which are operatively-linked to regulatory sequences (e.g., promoter sequences) but without additional vector sequences may be introduced into a host cell. As used herein, a host cell is intended to include any prokaryotic or eukaryotic cell or cell line so long as the cell or cell line is not incompatible with the protein to be expressed, the selection system chosen or the fermentation system employed. Exemplary examples of mammalian cell lines include, but are not limited to, those exemplified herein as well as CHO dhfr-cells (Urlaub and Chasin (1980) Proc. Natl. Acad. Sci. USA 77:4216 4220), 293 cells (Graham, et al. (1977) J. Gen. Virol. 36:59) or myeloma cells like SP2 or NSO (Galfre and Milstein (1981) Meth. Enzymol. 73 (B):3 46).

Soluble Sp1 may be produced in by a variety of non-mammalian eukaryotic cells as well, including insect (e.g., *Spodoptera frugiperda*), yeast (e.g., *S. cerevisiae, Schizosaccharomyces pombe, Pichia pastoris, Kluveromyces lactis, Hansenula Polymorpha* and *Candida albicans*, and fungal cells (*Neurospora crassa, Aspergillus nidulins, Aspergillus fumigatus*).

Nucleic acid sequences encoding Sp1 may be introduced into a host cell using standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, *Agrobacterium*-mediated transformation, cell fusion, and ballistic bombardment. Suitable methods for transforming host cells may be found in Sambrook, et al. (2001, Molecular Cloning: A Laboratory Manual, Cold Spring Harbor Laboratory Press, Cold Spring Harbor, N.Y.) and other laboratory manuals.

The number of host cells transformed with a nucleic acid sequence encoding Sp1 will depend, at least in part, upon the type of recombinant expression vector used and the type of transformation technique used. Nucleic acids may be introduced into a host cell transiently, or more typically, for long-term expression of Sp1, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acids of interest. Preferred selectable markers include those which confer resistance to certain drugs, such as G418 and hygromycin. Selectable markers may be introduced on a separate plasmid from the nucleic acids of interest or introduced on the same plasmid. Host cells transfected with nucleic acid sequences encoding Sp1 (e.g., a recombinant expression vector) and a gene for a selectable marker may be identified by selecting for cells using the selectable marker. For example, if the selectable marker encodes a gene conferring neomycin resistance, host cells which have taken up nucleic acid may be selected with G418 resistance. Cells that have incorporated the selectable marker gene will survive, while the other cells die.

A host cell transformed with nucleic acid sequences encoding Sp1 may be further transformed with one or more nucleic acids which serve as the target for Sp1.

Nucleic acid sequences encoding Sp1 may be introduced into cells growing in culture in vitro by conventional transformation techniques (e.g., calcium phosphate precipitation, DEAE-dextran transfection, electroporation, etc.). Nucleic acids may also be transferred into cells in vivo, for example by application of a delivery mechanism suitable for introduction of nucleic acid into cells in vivo, such as retroviral vectors (see e.g., Ferry, et al. (1991) Proc. Natl. Acad. Sci. USA 88:8377 8381; Kay, et al. (1992) Hum. Gene Ther. 3:641 647), adenoviral vectors (see e.g., Rosenfeld (1992) Cell 68:143 155; Herz and Gerard (1993) Proc. Natl. Acad. Sci. USA 90:2812 2816), receptor-mediated DNA uptake (see e.g., Wu and Wu (1988) J. Biol. Chem. 263:14621; Wilson, et al. (1992) J. Biol. Chem. 267:963 967; U.S. Pat. No. 5,166, 320), direct injection of DNA uptake (see e.g., Acsadi, et al. (1991) Nature 334:815 818; Wolff, et al. (1990) Science 247:1465 1468) or particle bombardment (see e.g., Cheng, et al. (1993) Proc. Natl. Acad. Sci. USA 90:4455 4459; Zelenin, et al. (1993) FEBS Let. 315:29 32).

Once produced, the Sp1 may be recovered from the culture medium as a secreted polypeptide, although it also may be recovered from host cell lysates when directly expressed without a secretory signal. When Sp1 is expressed in a recombinant cell other than one of human origin, the Sp1 is completely free of proteins or polypeptides of human origin. However, it is necessary to purify Sp1 from recombinant cell proteins or polypeptides to obtain preparations that are substantially homogeneous as to Sp1. As a first step, the culture medium or lysate is centrifuged to remove particulate cell debris. The membrane and soluble protein fractions are then separated. The Sp1 may then be purified from the soluble protein fraction. Sp1 thereafter is purified from contaminant soluble proteins and polypeptides, as exemplified herein or with, for example, the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; ligand affinity chromatography, and protein A Sepharose columns to remove contaminants such as IgG.

Standard protein separation techniques for purifying recombinant and naturally occurring proteins are well known in the art and include, but are not limited to solubility fractionation (such as salt fractionation or cold ethanol precipitation); size differential filtration (such as ultrafiltration through membranes of different pore size, e.g. Amicon or Millipore membranes); column chromatography (wherein the protein of choice can also be separated from other proteins on the basis of its size, net surface charge, hydrophobicity, and affinity for ligands, or by using antibodies raised against recombinant or naturally occurring proteins conjugated to column matrices). All of these methods are well known in the art.

Diagnostic Assays

The present invention has application in various diagnostic assays, including but limited to, the detection of DNA damage as a result of medical exposure to ionizing radiation and chemotherapeutic agents.

Based on the novel biological activities of Sp1, another embodiment of this invention is a method for simply and rapidly detecting DNA damage in a biological sample utilizing the above-mentioned Sp1. By "biological sample" is meant any mammalian cell or tissue, or cell or tissue-containing composition or isolate. For example, one biological sample may be a cell scraping, exudate or tissue specimen for biopsy, e.g., a buccal sample, sputum, cervical scraping. Another type of biological sample may be a preparation containing white blood cells, e.g., peripheral blood, sputum, saliva, urine, etc. for use in detecting the presence or absence of DNA damage in a patient that has been exposed to a DNA DSB inducing agent, such as radiation, chemicals, etc. Thus, the diagnostic method of this invention comprises contacting the biological sample, preferably immobilized or fixed on a surface, such as a microscope slide, with a ligand that binds to Sp1 when a phosphate moiety is present at serine residue 101. Such ligands are discussed in detail above, and are preferably associated with a label which provides a detectable signal, also as discussed above. The sample is then examined for the presence of signal concentrated in the cells of the sample. The examining step is any suitable assay step, including, without limitation, fluorescent immunomicroscopy or immunohistochemical analysis.

The presence of the antibody specifically binding Sp1 is indicative of DNA damage. Thus, this method is used to rapidly and easily identify cancer cells in conventional cancer screening and is used to monitor the status of anti-cancer therapies. Additionally, this method is also employed to rapidly and readily assess the possibility of DNA damage in patients exposed to gamma irradiation or other DNA damage agents, particularly those known to cause DNA DSBs.

Therapies

Phosphoserine$^{101}$ Sp1 can be administered to an individual as a therapeutic agent using any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of a slow release formulation. For treating tissues in the central nervous system, administration can be by injection or infusion into the cerebrospinal fluid (CSF). When it is intended that the active agent be administered to cells in the central nervous system, administration can be with one or more agents capable of promoting penetration of the active agent across the blood-brain barrier (see, e.g., Friden et al., 1993). Furthermore, Phosphoserine$^{101}$ Sp1, mutant Phosphoserine$^{101}$ Sp1, fragments of Phosphoserine$^{101}$ Sp1 or mutant Phosphoserine$^{101}$ Sp1 forms of such polypeptides, can be stably linked to a polymer such as polyethylene glycol to obtain desirable properties of solubility, stability, half-life and other pharmaceutically advantageous properties (see, e.g., Davis et al., 1978; Burnham, 1994).

Furthermore, the active agent can be in a composition which aids in delivery into the cytosol of a cell. For example, the peptide may be conjugated with a carrier moiety such as a liposome that is capable of delivering the peptide into the cytosol of a cell. Such methods are well known in the art (see, e.g., Amselem et al., 1993). Alternatively, the active agent can be modified to include specific transit peptides or fused to such transit peptides which are capable of delivering the Phosphoserine$^{101}$ Sp1, or fragment of phosphoserine$^{101}$ Sp1 of the present invention into a cell. In addition, such polypeptides can be delivered directly into a cell by microinjection.

The phosphatase inhibitors and activators, and kinase inhibitors and activators, can also be linked or conjugated with agents that provide desirable pharmaceutical or pharmacodynamic properties as described above, such as the coupling of the active substance to a compound which promotes penetration or transport across the blood-brain barrier or stably linking the active substance to a polymer to obtain desirable properties of solubility, stability, half-life and the like.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The active agent can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also contemplated that certain formulations containing the active agent may be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in light of the relevant circumstances including the condition or conditions to be treated, the choice of composition to be administered, the age, weight, and response of the individual patient, the severity of the patient's symptoms, and the chosen route of administration. Whereas typically the patient as referenced herein is human, nevertheless, the formulations and methods herein can be suitably prepared and used for veterinary applications in addition to human applications and the term "patient" as used herein is intended to include human and veterinary patients.

In a number of circumstances it would be desirable to determine the level of a phosphoserine$^{101}$ Sp1 with respect to the non-phosphorylated Sp1 in a cell. This would provide an assessment of the status of the cell and allow the design of a rational treatment program designed to change the level and/or ratio of phosphorylated to non-phosphorylated Sp1. A high level of phosphoserine$^{101}$ Sp1 might indicate an increase in DNA damage in the cell and could indicate the need for treatment to decrease the non-phosphorylated Sp1.

Furthermore, in the treatment of disease conditions, compositions containing Phosphoserine$^{101}$ Sp1 can be administered exogenously and it would likely be desirable to achieve certain target levels of phosphoserine$^{101}$ Sp1, as well as a ratio of non-phosphorylated to phosphorylated Sp1 in sera, in any desired tissue compartment or in the affected cells or tissue. It would, therefore, be advantageous to be able to monitor the levels of non-phosphorylated and phosphorylated Sp1 in a patient or in a biological sample, including a tissue biopsy sample obtained from a patient who was either exposed to IR or chemotoxic agents or is receiving radiotherapy or chemotherapy. Accordingly, the present invention also provides methods for detecting the presence of phosphoserine$^{101}$ Sp1, and the ratio of non-phosphorylated to phosphorylated Sp1, in a cell or a population of cells or in a sample from a patient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Cell Lines

Normal human diploid fibroblasts (NHDFs; Clonetic, Walkersville, Md.) were cultured in Dulbecco's Modified Eagle's Medium (DMEM, Cellgro, Mediatech, Inc., Herndon, Va.) with 10% fetal bovine serum (FBS; Equitech-Bio, Inc., Kerrville, Tex.), 2 mM L-glutamine (Cellgro, Mediatech, Inc., Herndon, Va.), and 100 U/mL penicillin, and 100 µg/mL streptomycin (Pen/Strep; Sigma, St. Louis, Mo.) in a 37° C. humidified atmosphere of 10% $CO_2$, 90% air. Osteosarcoma cells (U2OS) were cultured in Dulbecco's Modified Eagle's Medium (DMEM, Cellgro, Mediatech, Inc., Herndon, Va.) with 10% fetal bovine serum (FBS; Equitech-Bio, Inc., Kerrville, Tex.), 2 mM L-glutamine (Cellgro, Mediatech, Inc., Herndon, Va.), and 100 U/mL penicillin, and 100 µg/mL streptomycin (Pen/Strep; Sigma, St. Louis, Mo.) in a 37° C. humidified atmosphere of 10% $CO_2$, 90% air. Ataxia Telangiectasia-mutated untransformed fibroblasts from a clinically affected 15YO female homozygous for the 103C>T transition in exon 5 of the ATM gene (GM02052, Coriell) and untransformed fibroblasts from a clinically unaffected sister of the proband (GM03491, Coriell) were cultured in Minimum Essential Medium with Eagle-Earle salts (MEM, Cell-gro, Mediatech, Inc., Herndon, Va.) containing 15% FBS (Equitech-Bio, Inc. Kerrville, Tex.), 2 mM L-gluatmine, 1× non-essential amino acids (Sigma, St. Louis, Mo.), and Pen/Strep at 37° C. in a humidified atmosphere of 5% $CO_2$, 95% air. The M059J human glioblastoma cell line (ATCC) lacks DNA-dependent protein kinase activity while the M059K human glioblastoma cell line (ATCC) from the same donor expresses normal levels of active DNA-dependent protein kinase. These cells were cultured in DMEM/Ham's F-12 50/50 mix (Cellgro, Mediatech, Inc., Herndon, Va.) with 10% FBS (Equitech-Bio, Inc., Kerrville, Tex.), 2 mM L-glutamine and Pen/Strep at 37° C. in a humidified atmosphere of 10% $CO_2$, 90% air. Human papilloma virus-transformed cervical epithelial cells (HeLa, University of North Carolina Cell Culture Facility, Chapel Hill, N.C.) were cultured in Dulbecco's Modification of Eagle's Medium (DMEM, Cellgro, Mediatech, Inc., Herndon, Va.) containing 10% FBS (Equitech-Bio, Inc., Kerrville, Tex.), 2 mM L-glutamine (Cellgro, Mediatech, Inc., Herndon, Va.), and Pen/Strep at 37° C. in a humidified atmosphere of 5% $CO_2$, 95% air.

Cell Treatments $H_2O_2$ (30% w/w solution; Calbiochem, San Diego, Calif.) was added directly to the media of exponentially growing cells. In order to deliver an accurate volume, it was sometimes necessary to dilute the $H_2O_2$ in sterile water by a factor of 10 or 100. In these instances, the $H_2O_2$-water mix was prepared immediately before adding it to the cell media. Cells were exposed continuously to $H_2O_2$. For cells additionally exposed to Wortmannin (Biomol, Plymouth Meeting, Pa.), this agent was dissolved in DMSO (10 mM stock, 20 µM or 100 µM final) and added to the cell media 5-15 minutes prior to the addition of $H_2O_2$. KU55933 (provided by Graeme Smith of KuDOS Pharmeaceuticals LTD, Cambridge, UK) was dissolved in DMSO (10 mM stock, 10 µM final) and added one hour prior to addition of $H_2O_2$. For the experiments using ionizing radiation, exponentially growing cells were irradiated at room temperature using an X-ray source (dose rate of 3 Gy/min). For experiments using ultra-violet light, exponentially growing cells were irradiated at room temperature in a Stratalinker with UV-C (254 nm). Chemotherapeutic drugs were added directly to the media. Doxorubicin (Sigma, 5 mM stock in $H_2O$ diluted to 5 or 15 µM), Bleomycin (Biomol, 2.5 mg/mL stock in $H_2O$ diluted to 50-100 µg/mL), Etoposide (Biomol, 50 mM stock in DMSO diluted 5-20 µM), and Camptothecin (Biomol, 10 mM stock in DMSO diluted to 5-20 µM) were incubated with the cells for 1 hour. Hydroyurea (Sigma, 1M stock in $H_2O$ diluted to 0.05-2.5 mM) and Methotrxate (Calbiochem, 25 mg/mL stock diluted to 0.025-0.2 µg/mL) were incubated with cells for 24 hours.

In Vitro Phosphatase Treatment.

Sp1 was immunoprecipitated from NHDFs exposed to 200 µM $H_2O_2$ for one hour. Cells were lysed in ice-cold IP buffer (50 mM Tris 8.0, 0.5% Igepal, 120 mM NaCl, 1.5 mg/mL aprotinin, 0.01 mg/mL leupeptin, 1 mM PMSF). The chromatin was sheared by passing the lysate several times through a tuberculin syringe, and the lysate was cleared by centrifugation at 14,000×g for 10 minutes at 4° C. Approximately 500 µg of lysate was mixed with 8 µg Sp1-specific antibody (PEP-2G, Santa Cruz Biotechnology, Inc., Santa Cruz, Calif.). The mixture was incubated for one hour at 4° C. with rocking, followed by the addition of protein G slurry (Sigma, St. Louis, Mo.). After two hour incubation at 4° C. with rocking, immune complexes were washed three times in IP buffer, and incubated with or without 6 U calf intestinal alkaline phosphatase (1 U/µL; Promega Corporation, Madison, Wis.) for 40 minutes at 30° C., according to the manufacturer's instructions. The reaction was stopped by centrifuging the protein G slurry, removing the supernatant, and adding 2×SDS sample buffer to the immune complexes. Sp1 electrophoretic mobility was detected by immunoblot using an Sp1-specific antibody.

Phospho-Amino Acid Analysis.

NHDFs were plated at $1.5 \times 10^6$ cells in a 10 cm dish 24 hours before the experiment. On the day of the experiment, the cells were washed three times in 1×HBS. The cells were then incubated in phosphate-free DMEM supplemented with 10% dialyzed FBS for 2 hours at 37° C. NHDFs were then exposed to 200 μCi $^{32}$P-orthophosphate (NEN) per mL of media for 2.5 hours. NHDFs were then treated with 200 μM $H_2O_2$ for an additional hour. The cells were washed one time in 1×HBS and then harvested in 400 μL of lysis buffer [10 mM Tris pH=7.4, 1 mM O] and the plate was turned 90° counterclockwise and run in Hunter Thin Layer Peptide Mapping System at 1.3 kV for 20 minutes. The plate was allowed to air day after the second run then sprayed with DTT, 1% SDS]. The lysate was boiled at 95° C. for 6 minutes and 800 μL of cold IP buffer was added [15 mM Tris pH 7.4, 230 mM NaCl, 1.5% Triton X-100, 0.75% Igepal, 7.5 mM EDTA, 0.02 mg/mL leupeptin, 2 mg/mL pepstatin A, 3 μg/mL aprotinin, 2 mM PMSF, 15 mM NaF, 3 mM NaVO$_4$]. The lysate was sheared with a tuberculin syringe and centrifuged at 14K×g for 15 minutes at 4° C. The supernatant was transferred to a new tube and rocked with Sp1-specific antibody (pAb581, made against amino acids 524-543; Roswell Park Cancer Institute, Buffalo, N.Y.) for 30 minutes at 4° C. 25 μL protein A: Sepharose beads (Sigma, St. Louis, Mo.) were added and rocked overnight at 4° C. Beads were washed 3 times in 0.5 mL RIPA buffer. Samples were boiled in 30 μL 2×SDS sample buffer for 5 minutes at 90° C. Samples were resolved on 6.5% SDS-PAGE and transferred to PVDF membrane. Blots were exposed to film overnight. The band corresponding to the signal on the developed film was cut from the PVDF membrane. The excised membrane was washed in methanol one time and 4 times in water and transferred to a tube containing 200 μL of boiling HCl (Sigma, St. Louis, Mo.) and boiled for 1 hour at 110° C. Supernatant was transferred to a new tube and dried and resuspended in 5 μL pH1.9 buffer [50 mL formic acid, 156 mL glacial acid, 1794 mL dH$_2$O] and with 5 μL phosphoamino acid standards (1 mg/mL phosphoserine, phospho-threonine, phospho-tyrosine) added. The sample was added to a nitrocellulose plate (EM Science, Gibbstown, N.J.) in 0.5 μL drops and run in Hunter Thin Layer Peptide Mapping System at 1.5 kV for 25 minutes. After air drying the plate, it was rewet in pH 3.5 buffer [100 mL glacial acetic acid, 10 mL pyridine, 1890 mL dH$_2$ ninhydrin and baked at 65° C. for 10 minutes to visualize standards. The plate was exposed to a phosphoscreen for 24 hours.

Site-Specific Mutagenesis

Point mutations of various SQ sites located in the transactivation domains of Sp1 were made using the QuikChange Site-Directed Mutagenesis kit (Stratagene, La Jolla, Calif.). The following primer sequences in Table 1 were used.

TABLE 1

Primer sequences

| | | |
|---|---|---|
| SEQ ID NO.: 3 | S101A: | 5'-CCTCACAGCCACACAACTTGCACAGGGTGCCAA TGGC-3' |
| SEQ ID NO.: 4 | S101E: | 5'ACCTCACAGCCACACAACTTGAACAGGGTGCCAA TGGCTGG-3' |

TABLE 1-continued

Primer sequences

| | | |
|---|---|---|
| SEQ ID NO.: 5 | S291A: | 5'-GCAGCTCTGGGGCCCAGGAGAGTGGC-3' |
| SEQ ID NO.: 6 | S296A: | 5'-CCCAGGAGAGTGGCGCACAGCCTGTCACC-3' |
| SEQ ID NO.: 7 | S36A: | 5'GGTGGTGGTGCCTTTGCACAGGCTCGAAGTAG C-3' |
| SEQ ID NO.: 8 | S56A: | 5'-GGAGGGCAGGAGGCCCAGCCATCCC-3' |
| SEQ ID NO.: 9 | S313A: | 5'-GCCAGCTTGGTATCAGCACAAGCCAGTTCC-3' |
| SEQ ID NO.: 10 | S431A: | 5'-CCTTTACAACTCAAGCCATCGCCCAGGAAACC C-3' |
| SEQ ID NO.: 11 | S81,85A: | 5'-GAACAGCAACAACGCCCAGGGCCCGGCTCAGTC AGGGGAACAGGTGAGC-3' |

QuikChange PCR was performed on Sp1 cDNA with a C-terminal HA-tag subcloned into the pFLAG-CMV2 plasmid (Sigma, St. Louis, Mo.). PCR reactions were prepared according to the manufacturer's specifications. Recombinant colonies were screened for the appropriate mutation by fluorescent sequencing.

RNA Interference

We designed RNA oligonucleotides targeting the 3'UTR of Sp1 mRNA. The two targets are: 3'UTR$^{3429}$UCAGUGGAAUUGUACAAGA$^{3447}$ (SEQ ID NO.: 12) and 3'UTR$^{4974}$GGAAUCUUCUCCAGUAUGA$^{4992}$ (SEQ ID NO.: 13) of Sp1 mRNA (NCBI accession number NM_138473). These were tested separately and together and 200 pmoles (100 pmoles of each siRNA) were used together to transfect $2 \times 10^5$ cells per well of a 6 well plate in all experiments shown. As a non-targeting control siRNA, we altered siSp1 #1 by one nucleotide: GGAAUCUUCU ACAGUAUGA (SEQ ID NO. 15). This change created an siRNA that did not significantly reduce Sp1 levels. These double stranded RNA oligonucleotides were synthesized by Dharmacon, Inc. (Lafayette, Colo.).

Transfections

HeLa cells were transfected with wild-type and mutant Sp1 constructs in pFLAG-CMV2 using FuGENE 6 Transfection Reagent (Roche, Basel, Switzerland) or Lipofectamine 2000 (Invitrogen Corporation, Carlsbad, Calif.) according to manufacturers' instructions. Approximately 48 hours after transfection, cells were either exposed to $H_2O_2$ for one hour or left untreated. Cells were then harvested by direct lysis in 1.5×SDS sample buffer. For siRNA transfections, NHDFs were plated in 6-well plates 24 hours before transfection. Transfections were carried out using Oligofectamine Reagent (Invitrogen Corporation, Carlsbad, Calif.) according to the manufacturer's instructions. 72 hours after transfection, cells were assayed for the presence of Sp1 by immunoblot and indirect immunofluorescence.

Chromatin Salt Extraction

NHDFs were plated at $1.0 \times 10^7$ per 15 cm plate 24 hours before treatment with 200 μM $H_2O_2$ for 1 hour. Each plate was harvested in 3 mL of PBS-EDTA. Cell pellets were resuspended in 100 μL Buffer A [10 mM HEPES, pH 7.9, 10 mM KCl, 1.5 mM MgCl$_2$, 340 mM NaCl, 10% glycerol, 1 mM DTT, 5 μg/mL aprotinin, 5 g/mL leupeptin, 0.5 μg/mL pepstatin A, 0.1 mM PMSF]+0.1% Triton X-100. After 3 minutes incubation on ice, samples were centrifuged at 1,300×g for 4 minutes at 4° C. Supernatant was removed as cytoplasmic fraction; and nuclei were in the pellet. The pellet was resuspended in 20 μL of 1× Buffer B [3 mM EDTA, 0.2 mM EGTA, 5 μg/mL aprotinin, 5 μg/mL leupeptin, 0.5 μg/mL pepstatin A, 0.1 mM PMSF] and 30 μL of the resuspension was removed as nuclear extract. To the remaining nuclei pellet, 80 μL of 2× Buffer B was added followed by incubation on ice for 30 minutes. Samples were spun at 14,000×g for 4 minutes at 4° C. and supernatant was removed. The pellet was resuspended in 20 μL of 1× Buffer B and 80 μL of 2× Buffer B+125 mM KCl was added. Samples were incubated on ice for 30 minutes and centrifuged at 14,000×g for 4 minutes at 4° C. Supernatant was removed and designated as 125 mM KCl sample. The pellet was resuspended in 20 μL of 1× Buffer B followed by addition of 80 μL of 2× Buffer B+250 mM KCl. The sample was incubated on ice for 30 minutes and centrifuged at 14,000×g for 4 minutes at 4° C. Supernatant was removed and designated as 250 mM KCl sample. The chromatin pellet was resuspended in 20 μL of 1× Buffer B, subjected to one freeze/thaw, and then treated with 1 μg of DNase for 1 hour at 37° C. (Shi et al., 2004, Proc. Natl. Acad. Sci. U.S.A. 101:5898-903; Shirata et al., 2005, J. Biol. Chem. 280:30336-41). Samples were resolved on 6% SDS-PAGE and transferred to nitrocellulose and visualized by immunoblot as described below.

Electrophoretic Mobility Shift Assay

Nuclear extracts were prepared from U2OS cells untreated (−) or treated with 200 μM $H_2O_2$ for one hour. Cells were washed in 1×HBSS (8 g NaCl, 0.4 g KCl, 0.05 g $Na_2HPO_4$, 0.06 g $KH_2PO_4$, 0.75 mM spermidine, 0.15 mM spermine, and 1 mM DTT). Cells were scraped from the plate in 1×HBSS containing 0.0125M EDTA. Cells were spun at 800 rpm for 5 minutes at 4° C. Cells were resuspended in 5 pack cell volumes (PCV) of Buffer A (10 mM HEPES pH7.9, 0.1 mM EDTA pH8.0, 0.1 mM EGTA, and 10 mMKCl) and allowed to swell on ice for 10 min. Cells were then spun at 800 rpm for 5 minutes at 4° C. The pellet was then resuspended in 2 PCV of Buffer A and homogenized with a dounce, The cells were spun at 4,000×g for 2 minutes at 4° C. The nuclear pellet was the resuspended in 100 μL of Buffer C (20 mM HEPES pH7.9, 0.2 mM EDTA pH8.0, 2 mM EGTA, 20% glycerol, 0.75 mM spermidine, 0.15 mM spermine, 2 mM DTT and 1 mM PMSF). Then add 100 μL of Buffer C containing 0.75 NaCl dropwise to the suspension. The suspension is rotated at 4° C. for 20 minutes. The suspension is then spun at 50,000 rpm for 30 minutes and dialyzed two time for 90 minutes in Buffer D (20 mM HEPES pH7.9, 0.2 mM EDTA pH8.0, 2 mM EGTA, 100 mM KCl, 20% glycerol, 12.5 mM $MgCl_2$, 0.75 mM spermidine, 0.15 mM spermine, 2 mM DTT and 1 mM PMSF. For the EMSA, 4-8 μg of nuclear extract was incubated with 2 ug poly-dI-dC in 100 mM KCl, 2 μL 5× binding buffer (250 mM NaCl, 50 mM Tris pH7.9, 50% glycerol, 2.5 mM EDTA, 25 mM $MgCl_2$, 5 mM DTT, 300 μg/ml BSA) to a final volume of 10 μL. The mixture was incubated on ice for 10 minutes and then incubated with 10-30,000 cpm of labeled GC box probe for 5 minutes at room temp. The samples were separated on a 4.5% non-denaturing gel run at 20 mM for one hour. The bands were visualized by autoradiography.

Immunofluorescence

NHDF cells were plated onto glass coverslips 24 hours before treatment with 200 μM $H_2O_2$ or 2-5 Gy ionizing radiation. The in situ cell fractionation protocol was adapted from (Mirzoeva and Petrini, 2001, Mol. Cell. Biol. 21:281-8) with modifications. Briefly, cells were washed in ice-cold PBS twice and incubated in ice-cold cytoskeleton buffer (10 mM PIPES, pH 6.8; 100 mM NaCl, 300 mM sucrose, 3 mM $MgCl_2$, 1 mM EGTA) for 5 min, followed by incubation in ice-cold cytoskeleton stripping buffer (10 mM Tris-HCl pH 7.4, 10 mM NaCl, 3 mM $MgCl_2$, 1% v/v Tween 40, 0.5% sodium deoxycholate) for 5 min. Cells were then washed in PBS, and fixed using Streck Tissue Fixative (Streck Laboratories) with 50 mM EDTA, pH 5.7 (Kodym and Horth, 1995, Int. J. Radiat. Biol. 68:133-9) for 30 minutes at room temperature. Cells were washed 3 times in room temperature PBS and blocked in 10% FBS-PBS for one hour at room temperature. Primary antibody diluted 1:500 in 5% FBS-PBS solution was added and cells were incubated in this solution for one hour. Cells were washed in PBS five times followed by the addition of secondary antibodies AlexaFluor594 donkey anti-mouse antibody or with AlexaFluor488 donkey anti-rabbit antibody diluted 1:1000 in 5% FBS-PBS for 2 hours in the dark. Cells were washed 5 times with PBS. Slides were mounted using Vectashield mounting medium containing DAPI (Vector Labs, Burlingame, Calif.). Primary antibodies for indirect immunofluorescence included rabbit polyclonal anti-Sp1 (Upstate Biotechnology-Millipore Corporation, Billerica, Mass.) and mouse monoclonal γH2AX (ser139, Upstate Biotechnology-Millipore Corporation, Billerica, Mass.).

U2OS cells were plated onto glass coverslips 24-36 hours before treatment. Cells exposed to UV-A laser were incubated with 10 μM BrdU (10 mM stock, Sigma) for 24-36 hours prior to UV-A micro-irradiation. U2OS cells were washed in ice-cold PBS twice and pre-extracted in 0.2% Triton X-100/30% ddH2O/20 mM PMSF in PBS for 5 minutes at 4° C. Cells were then washed with PBS and fixed in 2% Para-formaldehyde/3% sucrose in PBS for 10 minutes at room temperature. Cells were washed twice in PBS at room temperature then permeablized in 0.5% Triton X-100 in PBS for 5 minutes at 4° C. Cells were washed 2 times in room temperature PBST (0.1% Tween 20, 0.02% Sodium azide in PBS) and incubated in primary antibody overnight at 4° C., mouse monoclonal γH2AX (ser139, Upstate Biotechnology), diluted 1:1000 in PBST solution, mouse P-ATMser1981 (Cell Signalling, diluted 1:1000) or rabbit polyclonal γSp1[101] (diluted 1:500, 21st Century Biotechnology). Cells were washed in PBST three times followed by the addition of secondary antibody, AlexaFlour488 donkey anti-rabbit, diluted 1:1000 in PBST and AlexaFlour594 donkey anti-mouse antibody, diluted 1:1000 in PBST for 1 hours in the dark. Cells were washed 4 times with PBST. Slides were mounted using Vectashield mounting medium containing DAPI (Vector Labs).

Immunoblot

Protein expression and modification were analyzed by immunoblot. Total cell lysates were prepared by either direct lysis of washed cells in 1.5×SDS sample buffer, or by non-denaturing cell lysis in 20 mM Tris-HCl, pH 7.8, 100 mM NaCl, 0.5% Igepal, 1 mM EDTA, 1.5 μg/mL aprotinin, 10 μg/1 mL leupeptin, 1 mM DTT, 1 μg/mL pepstatin A, 1 mM PMSF, 5 mM NaF, 5 mM β-glycerophosphate, and 0.1 mM $Na_3VO_4$ (each from Sigma). Cells lysed under non-denaturing conditions were incubated at 0-4° C. for 15-20 minutes and then transferred to microcentrifuge tubes. Chromatin was sheared by passing the lysate 3-4 times through a tuberculin syringe. Insoluble material was cleared by centrifugation at 14,000×g for 10 minutes at 4° C. Following protein quantitation by the Bradford method, 10-20 μg of protein was used for SDS-PAGE. Samples were electrophoresed at 150V in Tris glycine SDS running buffer (25 mM Tris, 192 mM glycine, 0.1% SDS, pH 8.3). Following electrophoresis, proteins were transferred to nitrocellulose membrane (Schleicher and Schuell) in Tris acetate transfer buffer. Immunoblot was performed by blocking membranes in 5% nonfat dried milk in PBS with 0.1% Tween-20 (PBST) followed by incubation with primary antibodies in 5% nonfat dried milk in PBST 14-18 hours at 4° C. with rocking with all antibodies, except γSp1[101] in which BSA (5%, Fraction V, Fisher Scientific, Pittsburgh, Pa.) was used. Primary antibodies used for immunoblot include rabbit polyclonal antibodies specific for Sp1 (pAb581, made at Roswell Park Cancer Institute against amino acids 524-543), and mouse monoclonal antibodies specific for γH2AX (phospho-Histone H2AX (Ser139), clone JBW301; Upstate Biotechnology-Millipore Corporation, Billerica, Mass.), total H2AX (Upstate Biotechnology-Millipore Corporation, Billerica, Mass.), α-Tubulin (Sigma, St. Louis, Mo.), nucleolin (C23; Santa Cruz Biotechnology, Santa Cruz, Calif.), and HA (HA.11; Covance, Princeton, N.J.), Phospho-Sp1$^{S101}$ was made by 21$^{st}$ Century Biochemicals, Inc. (Amherst, Mass.). SEQ ID NO.: 14 Acetyl-DL-TATQL[pS]QGANGK-amide produced a high affinity polyclonal antibody that specifically recognized phosphorylated S101; this antibody was designated γSp1[101]. The primary antibodies were detected with horseradish peroxidase-conjugated goat anti-rabbit IgG (Santa Cruz Biotechnology, Santa Cruz, Calif.) or goat anti-mouse IgG (Santa Cruz Biotechnology, Santa Cruz, Calif.). Chemiluminescence was developed using Super Signal (Pierce, Rockford, Ill.).

Cytotoxicity Assays

Clonogenic assays were performed as follows: $2.0 \times 10^5$ NHDFs or $4.0 \times 10^5$ U2OS were seeded in 30 mm dishes. In the case of NHDFs transfected with RNAi, cells were trypsinized and counted 72 hours after transfection. Cells were exposed to 50-100 μM $H_2O_2$ or 0.5-5Gy IR 18-24 hours after plating. 100 NHDFs were re-seeded onto 60 mm dishes 24 hours after exposure to $H_2O_2$ or 8 hours after exposure to IR. The cell media was changed every 3 days. Colonies, which formed between 18 and 24 days after plating for NHDF or 11 days after plated for U2OS, were fixed and stained with a crystal violet solution (0.5% in 20% Ethanol), and then counted. Assays were performed in triplicate.

In the case of the rescue experiment, U2OS cells were transfected with siRNA and replated 72 hours later. The cells were then transfected with WT Sp1 or Sp1-101A and 48 hours later cells were exposed to $H_2O_2$ and re-seeded onto 60 mm dishes. Colonies were fixed and stained in crystal violet 11 days after plating and then counted.

TUNEL Assay

U2OS cells were plated onto glass coverslips 24 hours before treatment with 400 μM $H_2O_2$. Cells were incubated for 4 hours and then processed for TUNEL staining following manufactures protocol (Chemicon). Briefly, cells were washed twice in PBS and fixed in 1% paraformaldehyde in PBS for 10 minutes at room temperature. Cells were washed twice in PBS and incubated in 2:1 mixture of ethanol:acetic acid at –20 degree Celsius for 5 minutes. Cells were washed twice in PBS and incubated in equilibration buffer for 10 seconds immediately followed by incubation with working strength TdT enzyme for one hour in humidified chamber at 37 degree Celsius. Cells were then incubated in Working Strength Stop/Wash Buffer for 10 minutes at room temperature. Slides were mounted using Vectashield mounting medium containing DAPI (Vector Labs).

Chromatin Immunoprecipitation

U2OS cells were plated 24 hours before the start of the experiment at $5.0 \times 10^6$ cells per dish. Cells were infected with HA-ER-I-PpoI for 24 hours then either untreated or treated with 4 μM 4-OHT (1 mM stock in ethanol, Sigma) for 16 hours. Cells were then cross-linked by adding 270 μL of 37% formaldehyde directly to the 10 mL of growth media for 10 minutes at room temperature. Cross-linking was quenched by the addition of glycine for 2 minutes at room temp. Cells were then washed once with ice-cold PBS and cells were scraped from plate in PBS, 1.5 μg/mL aprotinin, 10 μg/mL leupeptin, 1 μg/mL pepstatin A, 1 mM PMSF, 5 mM NaF, 5 mM β-glycerophosphate, and 0.1 mM $Na_3VO_4$ (each from Sigma). Cells were pelleted at 2000 RPM for 4 minutes at 4° C. and resuspended in SDS lysis buffer (1% SDS, 10 mM EDTA, 50 mM Tris pH 8.1, 1.5 μg/mL aprotinin, 10 μg/mL leupeptin, 1 μg/mL pepstatin A, 1 mM PMSF, 5 mM NaF, 5 mM β-glycerophosphate, and 0.1 mM $Na_3VO_4$). Cell lysis was incubated on ice for 10 minutes and sonicated with three 10 sec pulses at 26% power. Samples were then centrifuged at 13,000 RPM for 10 minutes at 4° C. and supernatant was diluted 10-fold in ChIP dilution buffer (0.01% SDS, 1.1% Triton X-100, 1.2 mM EDTA, 16.7 mM Tris-HCl, pH 8.1, 167 mM NaCl). The samples were precleared with 60 uL of salmon sperm DNA/Protein A agarose 50% slurry for 30 minutes at 4° C. Primary antibody (IgG, γSp1[101], or NBS1) was added and rocked overnight at 4° C. Salmon sperm DNA/Protein A agarose 50% slurry was then added for one hour at 4° C. The beads were then washed in low salt immune complex buffer (0.1% SDS, 1% Triton X-100, 2 mM EDTA, 20 mM Tris-HCl, pH 8.1, 150 mM NaCl), high salt immune complex buffer (0.1% SDS, 1% Triton X-100, 2 mM EDTA, 20 mM Tris-HCl, pH 8.1, 500 mM NaCl), lithium chloride immune complex buffer (0.25 M LiCl, 1% Igepal-CA630, 1% deoxycholic acid (sodium salt), 1 mM EDTA, 10 mM Tris, pH 8.1) and Tris-acetate buffer (10 mM Tris-HCl, 1 mM EDTA pH8.0). DNA was then eluted from beads for 15 minutes at room temperature in 1% SDS, 0.1M $NaHCO_3$. Cross-link was then reversed with 5M NaCl and samples were treated with RNase and Proteinase K. DNA was then isolated by phenol:chloroform extraction and PCR was performed with primers as described previously.

The results of these experiments are now described.

Experiment #1

Sp1 is Phosphorylated in Response to $H_2O_2$

ATM substrates possessing SQ/TQ cluster domains (SCDs) are collectively referred to as SCD proteins (Traven and Heierhorst, 2005, Bioessays 27:397-407). The most stringent classification requires a minimum of 5 SQ/TQ sites within a span of 50 residues with preferred phosphorylation sites generally preceded by a hydrophobic residue such as leucine (Kim et al., 1999, 274:37538-43; O'Neill et al., 2000, J. Biol. Chem. 275:22719-27). The Sp1 sequence spanning residues 56-102 easily fulfills this criterion, containing 5 SQ/TQ clusters within 47 amino acids. In addition, S101 is preceded by a leucine residue, suggesting this may be a preferentially targeted site of phosphorylation (FIG. 1). Sp1 also contains a second SCD domain that meets the less stringent Traven classification (5×SQ/TQ within 100 amino acids with a gap of less than 100 amino acids), possessing 9×SQ/TQ within a span of 147 residues (249-432). Interestingly, these domains both reside within Sp1's characterized transactivation domains, A and B (Courey and Tjian, 1988, Cell 55:887-98).

Based on the presence of putative SCDs in Sp1 and its reported association with DNA damage, it was determined whether Sp1 phosphorylation was stimulated by DNA damage. Cells were treated with hydrogen peroxide. $H_2O_2$, a relatively stable reactive oxygen species (ROS) that diffuses freely into cells, and the resulting increase in intracellular ROS production leads to the induction of varied DNA damage, including DSBs (Reberfroid and Calderon, 1995, Free Radicals and Oxidation Phenomena in Biological Systems. Marcel Dekker, Inc., New York).

Figure 2:
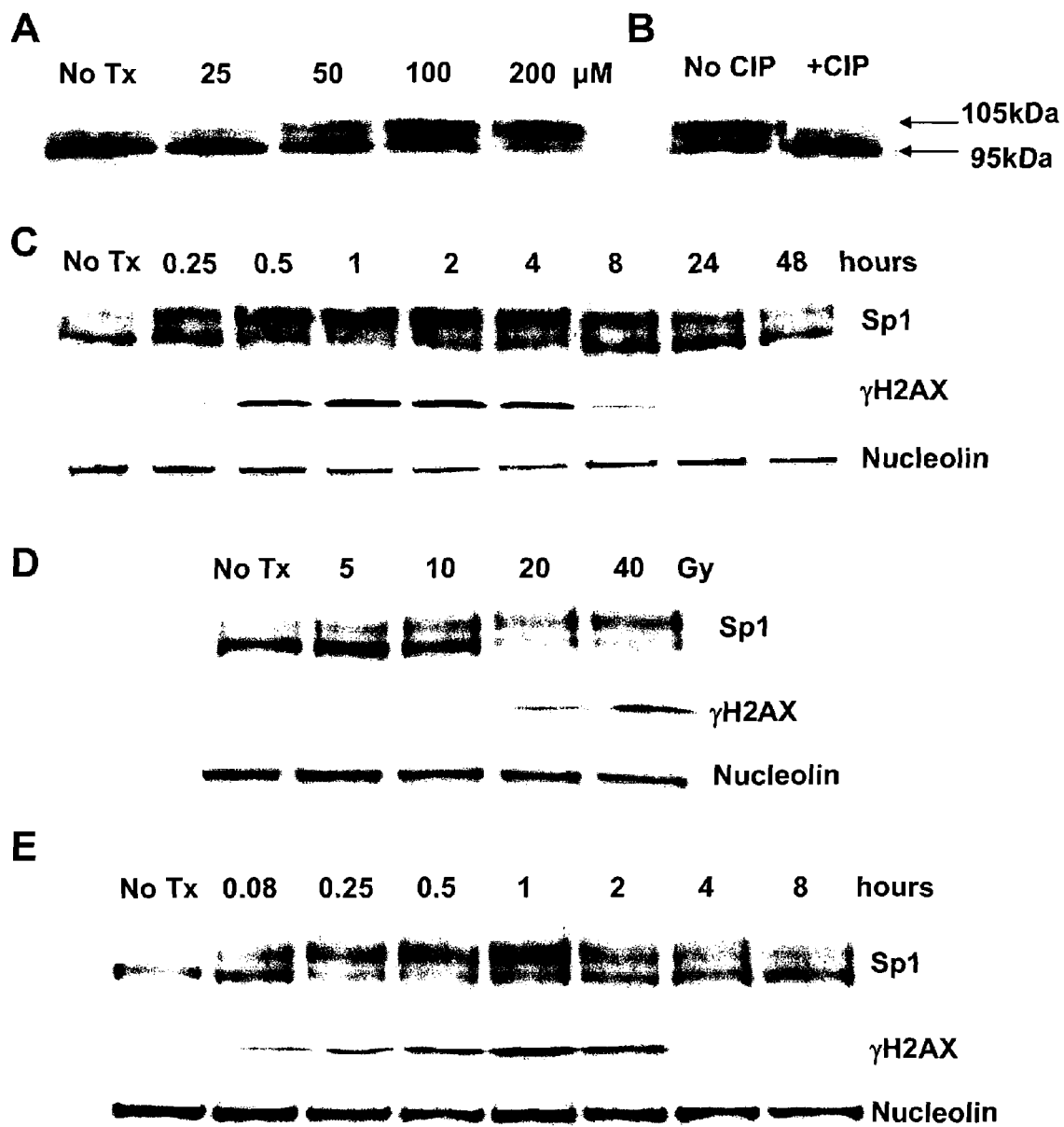
FIG. 2, comprising

Normal human diploid fibroblasts (NHDFs) in mid-log phase were exposed to $H_2O_2$, and total cell lysates were prepared after one hour. Cellular lysates were assayed for Sp1 phosphorylation by immunoblot. Phosphorylation of Sp1 has been reported to induce a shift in electromobility of Sp1 from 95 to 105 kDa (Jackson et al., 1990, Cell 63:155-65). Sp1 from untreated cells migrates in SDS-PAGE as a major species of 95 kDa and a minor species of 105 kDa. The shift to 105 kDa was found to be concentration-dependent; it is detected in cells exposed to 50 µM $H_2O_2$, and becomes the major Sp1 species in cells exposed to 200 µM $H_2O_2$ (FIG. 2A). To verify this shift in Sp1 migration was due to phosphorylation, immunoprecipitated Sp1 from $H_2O_2$ treated cells was incubated with phosphatase and analyzed by Sp1 immunoblot. As shown in FIG. 2B, treatment with phosphatase resulted in the loss of the 105 kDa form and increase in the 95 kDa form.

The kinetics of Sp1 phosphorylation after $H_2O_2$ treatment were then investigated. Extracts of NHDFs were prepared at various time points following exposure to 200 µM $H_2O_2$. Phosphorylation was observed as quickly as 15 minutes post-treatment, reaching peak levels at one hour (FIG. 2C). The change in the phosphorylation of Sp1 was also found to be transient, as the 95 kDa form of Sp1 became the predominant species by 8 hours. Changing media to remove $H_2O_2$ after one hour had no effect on the level of phosphorylation or the kinetics therefore media was not changed in subsequent experiments (data not shown). Taken together, these phosphorylation kinetics are consistent with those observed for other ATM substrates (Tibbetts et al., 1999, Genes Dev. 13:152-7), suggesting that Sp1 may be a target of the Sp1 pathway.

Experiment #2

The ATM Pathway Mediates the Phosphorylation of Sp1.

To characterize the relationship between $H_2O_2$-induced DSB induction, ATM activation, and Sp1 phosphorylation, the PIKK-dependent phosphorylation of the histone variant H2AX was examined (Rogakou et al., 1998, J. Biol. Chem. 273:5858-68; Rothkamm and Lobrich, 2003, Proc. Natl. Acad. Sci. U.S.A. 100:5057-62). Immunoblot analysis revealed the rapid phosphorylation/dephosphorylation of H2AX with kinetics paralleling the transient phosphorylation of Sp1 (FIG. 2C).

To further establish a link between DSBs, activation of ATM and phosphorylation of Sp1, cells were also treated with IR. As shown in FIGS. 2D and 2E, exposure of NHDF cells to IR induced the phosphorylation of Sp1, with greater radiation doses resulting in a shift to the 105 kDa form. Phosphorylation was detected within 5 minutes, with the 105 kDa form of Sp1 predominating for approximately 2 hours. This transient shift in Sp1 phosphorylation paralleled transient phosphorylation of H2AX.

Figure 3:
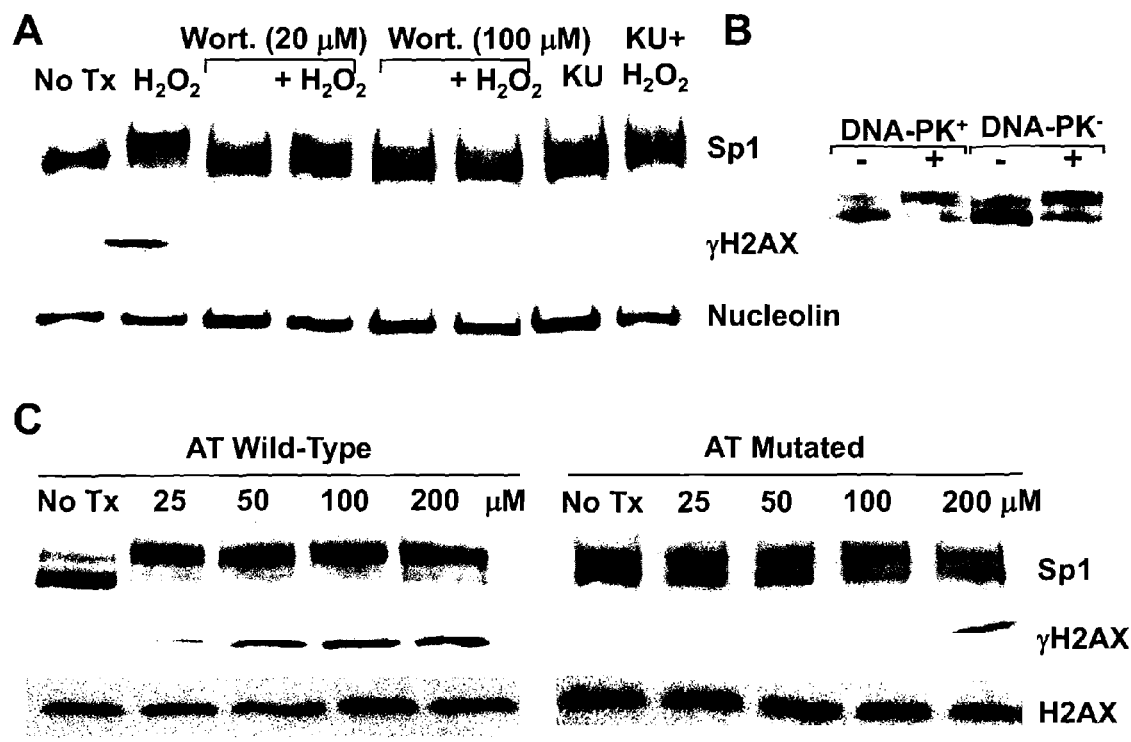
FIG. 3, comprising

Oxidative stress and IR induce the PIKK family, ATM, ATR and DNA-PK. To identify the signaling pathway(s) involved in mediating Sp1 phosphorylation in response to DNA damage, the effect of wortmannin and KU55933, a recently developed specific ATM inhibitor, was tested (Hickson et al., 2004, Cancer Res. 64:9152-9). Wortmannin inhibits ATM but not ATR at 20 µM, (Abraham, 2004, DNA Repair 3:883-7), whereas higher doses inhibit ATM, ATR, and DNA-PK. Phosphorylation of Sp1 and H2AX in response to $H_2O_2$ was not detected in cells pretreated with 100 µM wortmannin; however after pre-treatment with 20 µM wortmanin or 10 µM KU55933, $H_2O_2$-induced phosphorylation was reduced but not abolished (FIG. 3A). To more directly assess the role of DNA-PK, which phosphorylates Sp1 in vitro (Jackson et al., 1990, Cell 63:155-65), in the peroxide-induced phosphorylation of Sp1, cell lines with and without functional DNA-PK were exposed to $H_2O_2$ and found no difference in Sp1 phosphorylation (FIG. 3B).

Next, Sp1 and H2AX phosphorylation were compared in fibroblasts lacking functional ATM with wild-type fibroblasts from a related donor. In the fibroblasts with wild-type ATM, Sp1 was shifted completely to the 105 kDa form following a one hour exposure to 25 µM $H_2O_2$ (FIG. 3C). In cells lacking functional ATM, there is a very low level of phosphorylation of Sp1 that is not concentration-dependent and phosphorylation of H2AX was only detected when these cells were exposed to a higher level of $H_2O_2$. Since ATR and ATM have similar substrate specificities, ATR may be responsible for the observed phosphorylation of Sp1 at high levels of damage and at later time points in cells lacking functional ATM. Similar results were obtained from studies of p53 phosphorylation following IR exposure in AT-mutated cells, in which the delayed phosphorylation was attributed to ATR (Tibbetts et al., 1999, Genes Dev. 13:152-7). Our findings support the notion that the phosphorylation of Sp1 rapidly induced by $H_2O_2$ is ATM-dependent.

Experiment #3

Sp1 is Phosphorylated on S101 in Response to DNA Damage

Figure 4:
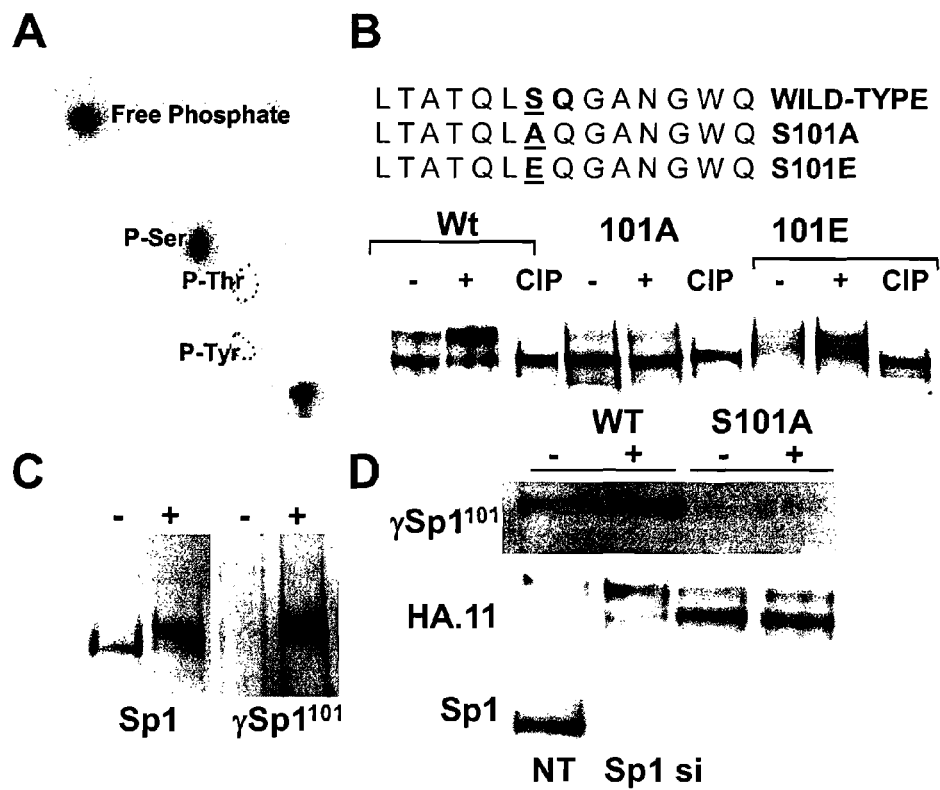
FIG. 4, comprising

PIKKs, like other kinases that reportedly phosphorylate Sp1, phosphorylate serine and/or threonine residues (Chu and Ferro, 2005, Gene 348: 1-11). As shown in FIG. 4A, Sp1 was primarily phosphorylated on serine(s) following $H_2O_2$ exposure. Based on the presence of two distinct SCDs and our phospho-amino acid results, mutations were made in nine serine residues within Sp1's two SCDs (36/56/81/85/101/291/313/296/431) either alone or in various combinations. To examine the phosphorylation of these residues in the context of DNA damage, HeLa cells were transfected with expression vectors encoding either HA-Sp1$^{WT}$ or with Ser[P] Ala substitutions. Most of these mutations had little or no effect on Sp1 phosphorylation in response to DNA damage (data not shown). In contrast, the Sp1$^{S101A}$ mutant remained largely at 95 kDa following $H_2O_2$ treatment while the HA-Sp1$^{WT}$ shifted to 105 kDa as expected (FIG. 4B). S101 was also replaced by glutamic acid as a phospho-mimic. Interestingly, Sp1$^{S101E}$ migrated with slower mobility even in the absence of damage. Treatment with phosphatase resulted in a mobility shift of Sp1$^{S101E}$ to the 95 kDa form, indicating that the altered mobility was due to phosphorylation rather than a structural alteration resulting from the mutation. These results are consistent with the hypothesis that phosphorylation of S101 is a priming event that signals additional phosphorylation.

In order to verify that S101 is phosphorylated in response to DNA damage, a phospho-specific antibody that specifically recognizes phosphorylated S101 was generated by 21$^{st}$ Century Biochemicals, Inc. (Amherst, Mass.). In immunoblot experiments, this antibody, designated γSp1$^{101}$, detects Sp1 in cells treated with $H_2O_2$ but does not detect Sp1 in untreated cells (FIG. 4C). Further, in cells depleted of endogenous Sp1 by siRNA, exogenously expressed WT HA-Sp1 is detected by γSp1$^{101}$, whereas Sp1$^{S101A}$ and Sp1$^{S101E}$ are not (FIG. 4D). Taken together, these data strongly support that S101 is phosphorylated in response to DNA damage and that its phosphorylation is required for additional phosphorylation.

Experiment #4

Enhanced Association of Sp1 with Chromatin Following DNA Damage

Figure 5:
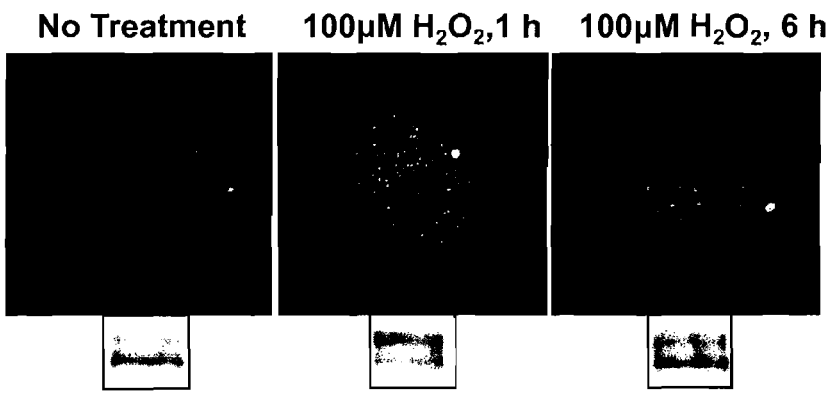
FIG. 5, comprising
Figure 5:
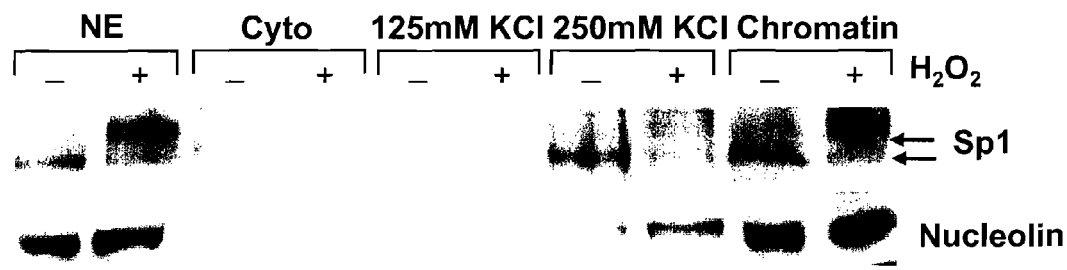
Figure 5:
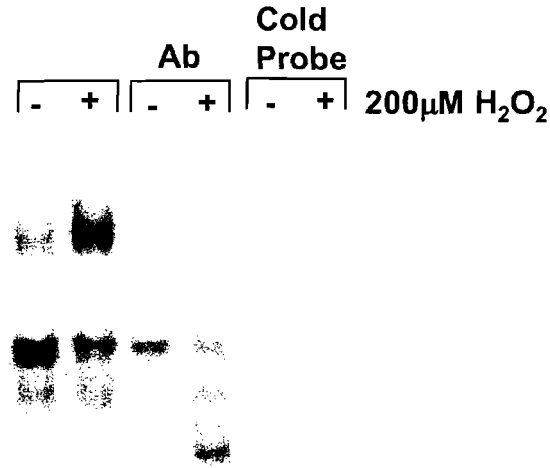

Several reports suggest that Sp1 DNA binding is increased by DNA damage (Meighan-Mantha et al., 1999, Mol. Cell. Biochem. 199:209-15; Ryu et al., 2003, J. Neurosci. 23:3597-606; Yang et al., 2000, FASEB J. 14:379-90). To determine whether DNA damage-induced phosphorylation of Sp1 correlates with an increased association with chromatin, a protocol involving detergent extraction prior to fixation was used for indirect immunofluorescence analysis of chromatin-associated Sp1 (Mirzoeva and Petrini, 2001, Mol. Cell. Biol. 21:281-8). This protocol allows detection of protein-chromatin associations that might otherwise be obscured by background immunofluorescence of soluble epitopes. Sp1 staining in untreated cells is micropunctate and relatively dim, indicating that the detergent extraction protocol removed a significant amount of Sp1. In contrast, Sp1 immunostaining appears brighter and localized to discrete foci in NHDFs exposed for one hour to 100 μM $H_2O_2$. The appearance of foci occurs when Sp1 is predominantly phosphorylated (FIG. 5A), suggesting that phosphorylation induced by DNA damage increases chromatin association. By six hours, chromatin association was decreased, correlating with the return of Sp1 to a dephosphorylated state (FIG. 5A).

An alternative approach to verifying Sp1's increased association with chromatin was to examine binding affinity by exploring the effect of damage on its extraction from chromatin. NHDFs were exposed to $H_2O_2$ for one hour followed by separation of cytoplasmic and nuclear components. Nuclear fractions were washed with buffers of increasing salt concentration (125 mM and 250 mM KCl, respectively) to release chromatin-bound protein complexes (Mendez and Stillman, 2000, Mol. Cell. Biol. 20:8602-12). Fractions were subsequently analyzed by immunoblotting with antibody to Sp1. As shown in FIG. 5B, Sp1 was extracted with 125 and 250 mM KCl more readily from untreated cells than from $H_2O_2$-treated cells. Moreover, Sp1 remained bound to chromatin after extraction with 250 mM KCl only in the treated cells and the remaining Sp1 was largely phosphorylated. These data demonstrate an increased association between Sp1 and chromatin in response to $H_2O_2$ exposure.

In addition to the chromatin extraction, electrophoretic mobility shift assays was used to determine Sp1's ability to bind to its DNA consensus sequence in cells exposed to $H_2O_2$. Nuclear extracts were prepared from untreated (−) and treated cells (+). The nuclear extracts were incubated with radiolabeled GC rich probe and separated by non-denaturing gel. As seen in FIG. 5C, in the presence of damage there is an increase in Sp1 binding to the consensus sequence. The binding can be inhibited in both untreated and treated sample by the addition of an antibody specific to Sp1 (581: Ab) or by incubating the reaction with an excess of un labeled probe (cold probe). This shows that the binding of Sp1 to its consensus sequence is specific.

Experiment #5

DNA Damage Induces Sp1 Foci

Figure 6:
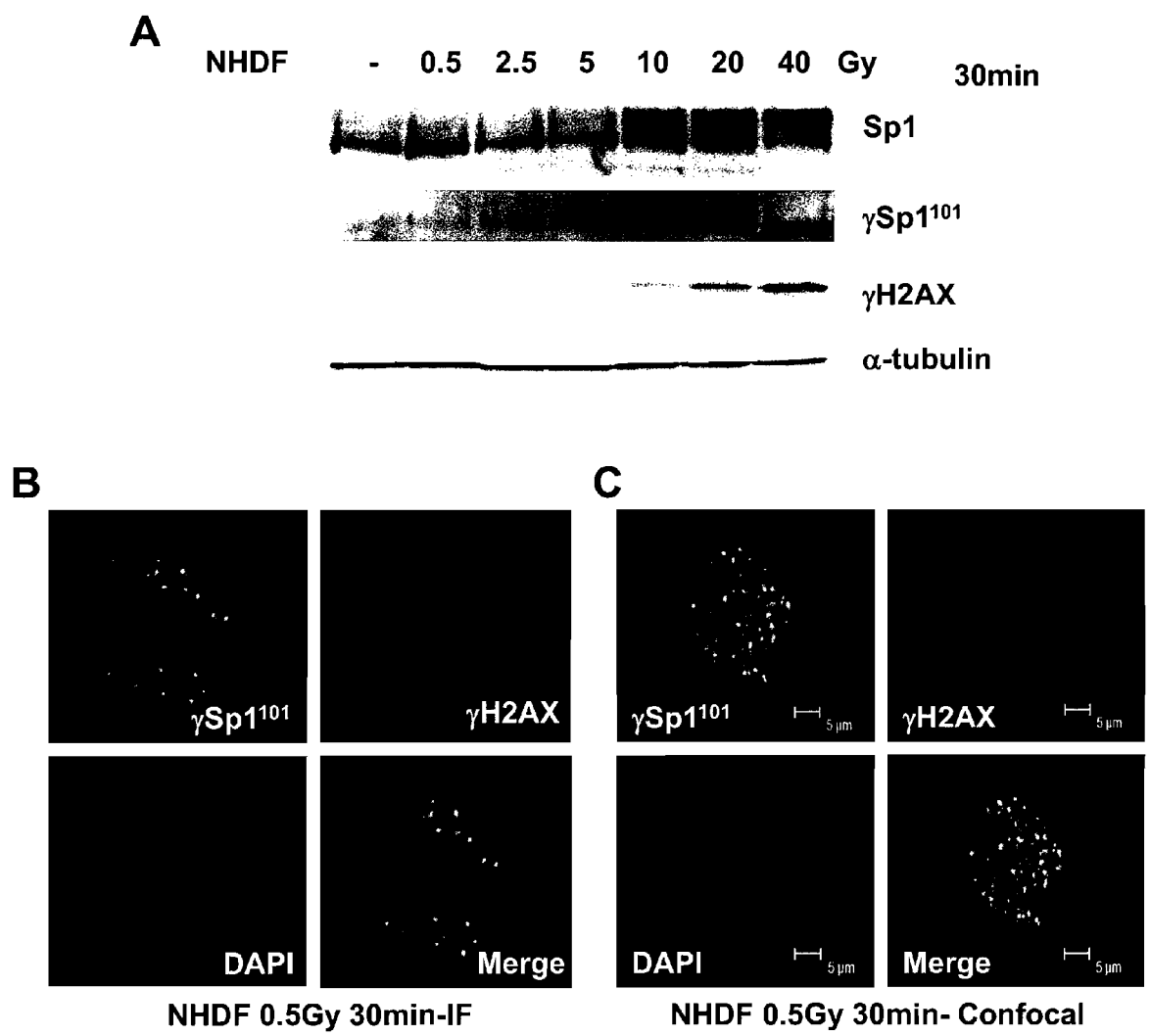
FIG. 6, comprising

Based on these findings that Sp1 is phosphorylated by ATM in response to DNA damage and that the phosphorylation is coincident with H2AX phosphorylation, immunofluorescence was performed to examine the localization of Sp1 relative to phospho-H2AX. In response to DNA DSBs, H2AX is phosphorylated over megabase-length stretches of chromatin flanking DSB sites and is thought to be involved in the recruitment of DNA damage response factors to the break site (Bartek and Lukas, 2007, Curr. Opin. Cell. Biol. 19:238-45). This can be detected as foci in immunofluorescence assays utilizing an antibody to phospho-H2AX (γH2AX). NHDFs varying concentration of IR and harvested after 30 min. As can be seen in FIG. 6A, the detection of phosphorylated Sp1 is seen with as little as 0.5 Gy or IR. The immunoblot detection of phosphorylated Sp1 at serine 101 is at a significantly lower dose then the standard marker of DNA double strand breaks, γH2AX. However, both are detected by immunofluorescence at this low dose (FIGS. 6B and C). NHDFs were exposed to 0.5 Gy IR and processed 30 minutes after exposure using the detergent extraction protocol and antibodies to γSp1$^{101}$ and γH2AX. As seen in FIGS. 6A and 6B, Sp1$^{101}$ co-localizes with γH2AX in IRIF.

Experiment # 6

Sp1 Depletion Renders Cells More Sensitive to DNA Damage

Figure 7:
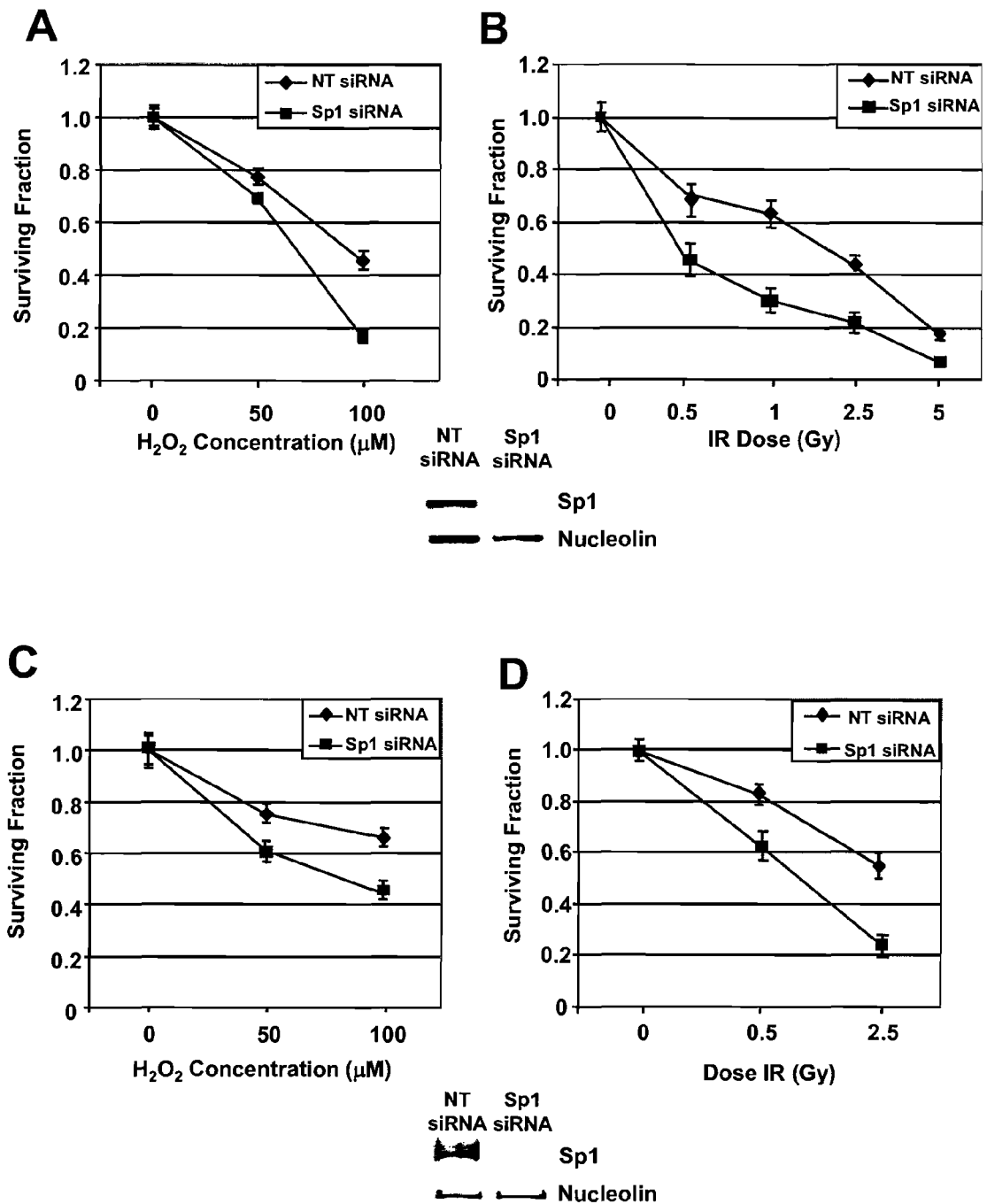
FIG. 7, comprising FIG. 7A through FIG. 7D is a series of graphs depicting how Sp1 knockdown decreases cell survival following ionizing radiation (IR) or $H_2O_2$ exposure in NHDF or U2OS cells.

To determine whether Sp1 modulates the cellular response to DNA damage, cells were depleted of Sp1 using siRNA. The effect of Sp1 on cell survival following exposure to IR or $H_2O_2$ was then assessed by clonogenic survival assays in NHDF and U2OS cells. Transfection of double-stranded siRNA oligonucleotides targeting the 3'UTR of Sp1 mRNA into NHDF and U2OS cells resulted in a 90% knockdown of Sp1 protein levels 3 days post-transfection (FIG. 7, inset). Cell morphology and growth were not significantly perturbed by Sp1 siRNA (data not shown). To assess the sensitivity of Sp1-deficient cells in response DNA damage, we compared the viability of cells transfected with non-targeting siRNA to Sp1 siRNA-transfected cells by clonogenic assays following exposure to IR and $H_2O_2$. Cells depleted of Sp1 demonstrated decreased colony formation following exposure to 0.5Gy to 5Gy IR relative to a non-targeting control siRNA (FIG. 7B and FIG. 7D). Similarly, cells depleted of endogenous Sp1 exposed to 50 μM or 100 μM $H_2O_2$ also demonstrated decreased colony formation relative to cells transfected with a non-targeting siRNA (FIG. 7A and FIG. 7C).

Experiment #7

Figure 8:
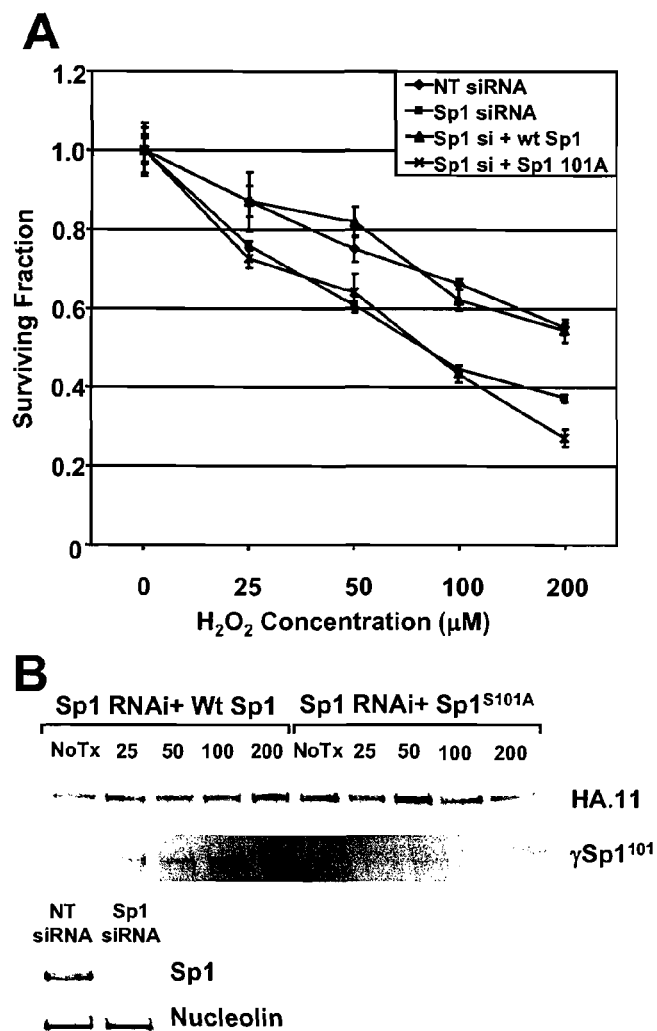
FIG. 8, comprising

Rescue of Increase Sensitivity to DNA Damage with Wild Type Sp1 not Phospho-Mutant Experiments were next performed to determine whether the increased sensitivity of cells after Sp1 depletion by RNAi was related to Sp1 phosphorylation. Colony survival assays were performed in U2OS cells, which can be effectively transfected with exogenous Sp1 (~60%) as compared to fibroblasts. Sp1 is phosphorylated on serine 101 in U2OS cells exposed to varying concentrations of $H_2O_2$ in a manner similar to NHDF as seen by γSp1$^{101}$ antibody (FIG. 8B). As shown in FIG. 8A, Sp1 depletion by Sp1 RNAi inhibited colony survival of U2OS cells in response to $H_2O_2$ in a concentration dependent manner. Expression of wild-type Sp1 restored survival to the level observed with non-targeting RNAi, rescuing cells from the effect of Sp1 depletion at every concentration of $H_2O_2$ tested. In contrast, expression of $Sp1^{S1014}$ (which is not phosphorylated in response to damage) failed to rescue cells from the effects of Sp1 depletion on survival. Expression level of Wt Sp1 and $Sp1^{1014}$ is shown in FIG. 8B. These results demonstrate that the phosphorylation of Sp1 on serine 101 by ATM plays an important role in modulating the cellular response to DNA damage.

Experiment #8

GC-rich regions are unusually sensitive to DNA damage by alkylating agents and represent more open regions of chromatin (Kundu and Rao, 1999, J. Biochem. 125:217-22; Mattes et al., 1988, Carcinogenesis 9:2065-72; Pfeiffer et al., 2000, Mutagenesis 15:289-302; Surralles et al., 2002, Proc. Natl. Acad. Sci. U.S.A. 99:10571-4). Based on this and the finding of enhanced Sp1 chromatin association after $H_2O_2$ or IR, the effect of Sp1 on the induction of DSBs by IR was determined. NHDF and U2OS cells were transfected with siRNA, followed by treatment with low dose IR (0.5Gy). Cells were processed for immunofluorescence 10 minutes, 4 hours and 16 hours after exposure. As shown in FIG. 9A and FIG. 9C, γH2AX foci were observed 10 minutes and 4 hours after treatment of cells depleted of Sp1 with siRNA exposed to IR, whereas foci were much less frequent and fewer in number in cells pre-treated with a non-targeting control siRNA. Foci were counted in at least 30 cells in a blinded fashion and an average of 7 foci per cell were observed 10 minutes after treatment of the cells depleted of Sp1 as compared with <2 foci for the control cells (FIG. 9B). The number of γH2AX foci observed in Sp1-depleted cells was significantly higher than in cells exposed to a non-targeting siRNA at all time points. Taken together with the correlation between the induction of Sp1 phosphorylation and increased chromatin binding and the appearance of Sp1 foci, these data suggest that Sp1 may play a role in protecting DNA from the induction of DSBs by IR.

Experiment #9

Figure 9:
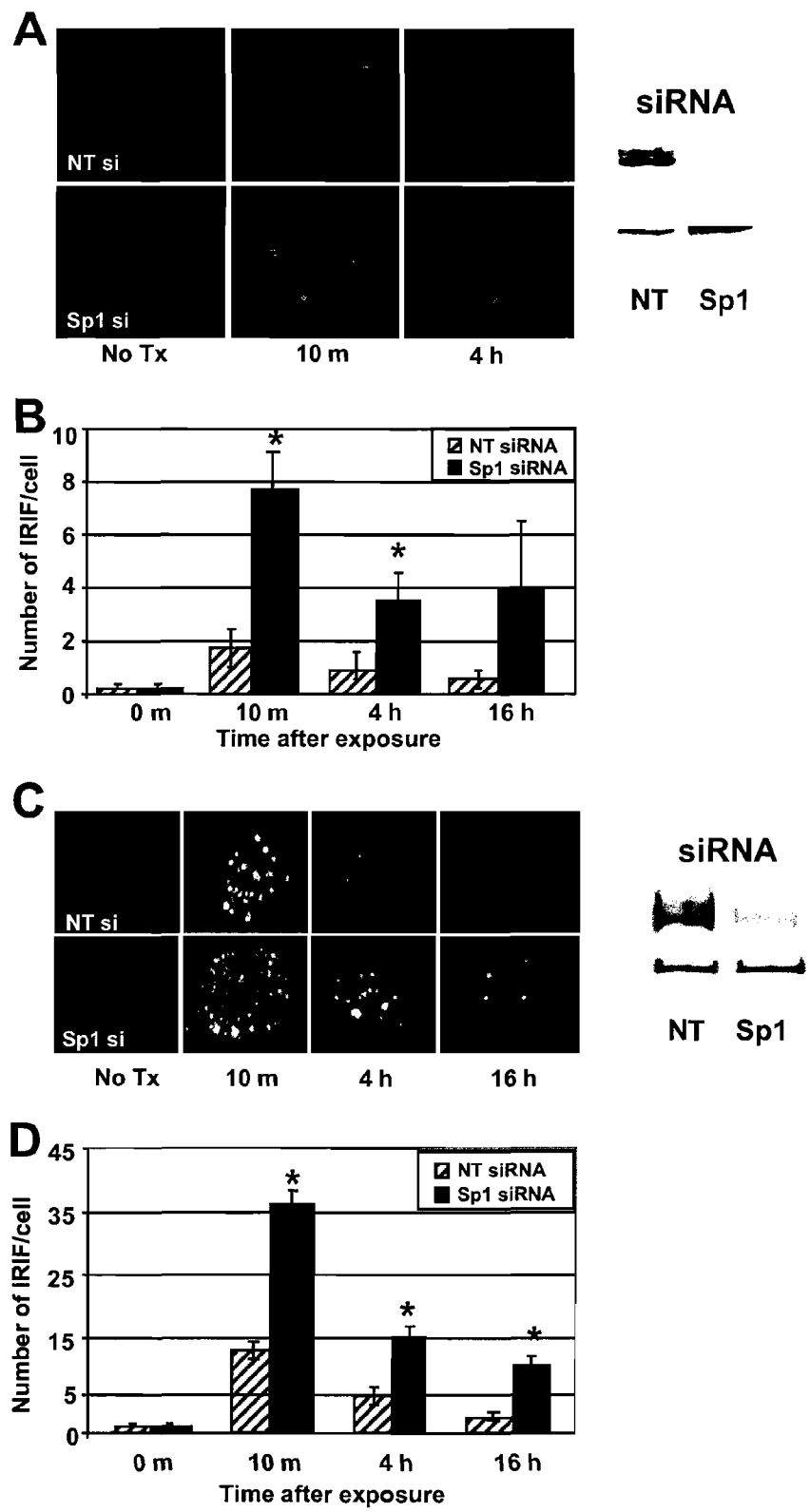
FIG. 9, comprising
Figure 10:
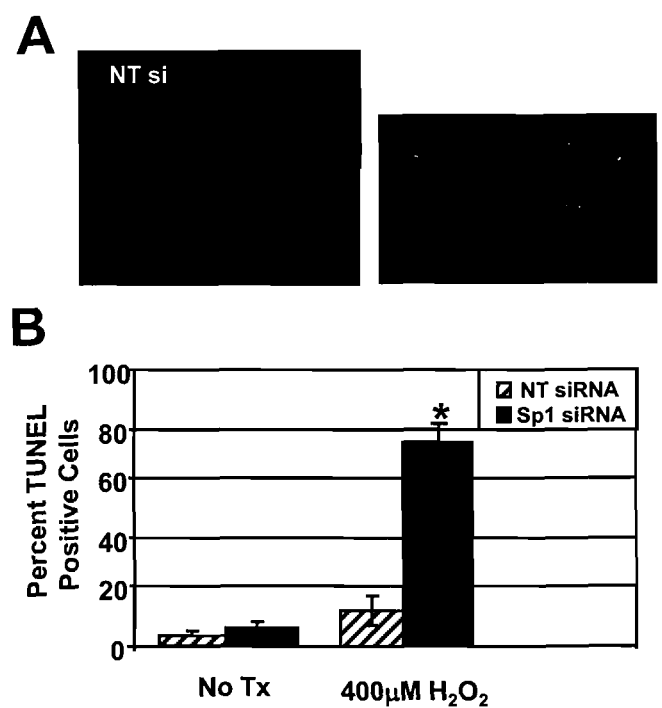
FIG. 10, comprising

To verify the decrease in cell viability in the colony assays were a result of an increase in apoptosis in cells depleted of Sp1 with siRNA as compared to non-targeting control siRNA, the TUNEL assay were performed in U2OS cells. U2OS cells were used in this assay because fibroblasts do not normally undergo apoptosis, but enter senescence. U2OS cells were transfected with siRNA, followed by treatment with 400 μM $H_2O_2$ for 4 hours. Cells were processed for immunofluorescence and as shown in FIG. 10A, cells depleted of Sp1 with siRNA after treatment are TUNEL positive demonstrated fragmented DNA, whereas cells transfected with a non-targeting control siRNA after treatment show less fragmented DNA. Quantification of these results demonstrate that 76% of cells depleted of Sp1 with siRNA are TUNEL positive compared to 10% of cells transfected with non-targeting control siRNA (FIG. 10B). The statistically significant (p<0.01) increase in DNA fragmentation in cells depleted of Sp1 with siRNA correspond to the increase in γH2AX foci and the decrease cell viability seen in the cells (FIG. 7 and FIG. 9).

Experiment #10

Figure 11:
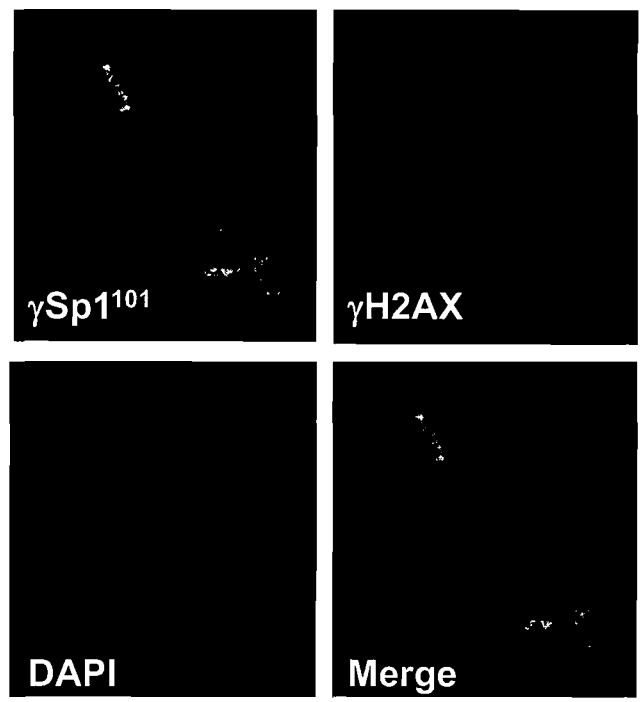
FIG. 11 is a series of images that depicts γSp1[101] (top left panel) and γH2AX (top right panel) co-localization to laser induced sites of damage (bottom right panel). U2OS cells were pre-incubated with 10 μM BrdU for 24 hours before being exposed to UV-A laser. Immunofluorescence images demonstrate localization of phosphorylated Sp1 to the site of damage along with phosphorylated H2AX.

To further investigate Sp1's localization to sites of DNA double strand breaks, we used laser micro-irradiation (i.e stripes). U2OS cells were incubated with 10 μM BrdU before exposure to UV-A laser. Cells were processed for immunofluorescence at 30 minutes after laser treatment. As can be seen in FIG. 11, $γSp1^{101}$ is recruited to the site of damage (ie the stripe) along with γH2AX.

Experiment #11

Figure 12:
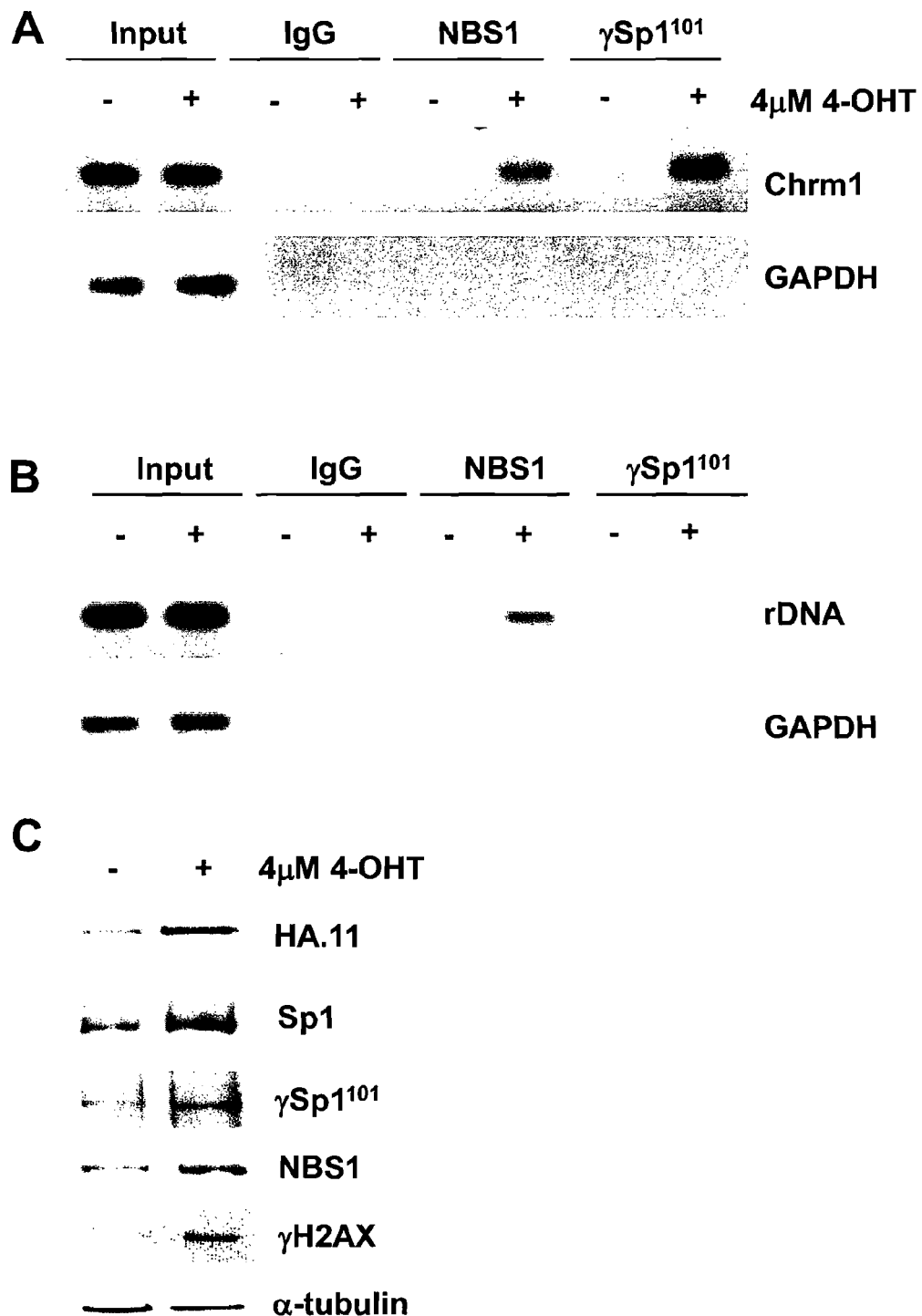
FIG. 12, consisting of FIG. 12A through FIG. 12C, is a series of images that depict the recruitment of phosphorylated Sp1 to specific sites of DNA damage.

The IRIF indicate protein localization in the vicinity of double strand break sites. In fact, γH2AX has been shown by chromatin immunoprecipitation (ChIP) to be localized as much as 1 megabase away from the actual site. To determine if Sp1 was recruited to the actual site of the DSB, a restriction enzyme expression plasmid was used with naturally occurring cut sites within the genome, I-PpoI. I-PpoI cuts at 15 base pair sequence (CTCTCTTAAGGTAGC; SEQ ID NO. 16) that is found in 28S ribosomal DNA and in the DAB1 gene promoter on chromosome 1 (Muscarella, et al., 1990, Mol. Cell. Biol. 10:3386-96, Flick, et al., 1998, Nature 394:96-101). ATM, NBS1, and γH2AX have previously been shown to localize at or in the vicinity of DSBs induced by the expression of I-PpoI (Berkovich, et al. 2007, Nature Cell Biol. 9:683-90). U2OS cells were infected with HA-ER-I-PpoI and then treated with 4 μM 4-OHT to induce the expression of the plasmid. Sixteen hours after treatment with 4-OHT, U2OS cells were cross-linked with formaldehyde and immunoprecipitated with antibody specific for phosphorylated Sp1 ($γSp1^{101}$) or NBS1. The DNA isolated from the chromatin immunoprecipitation was used in PCR reactions with primers to sites surrounding I-PpoI cut sites. The primers are as previously described (Berkovich, et al. 2007, Nature Cell Biol. 9:683-90). FIG. 12C shows the induction of expression of HA-ER-I-PpoI after treatment with 4-OHT and the expression levels of total Sp1 as well as $γSp1^{101}$, NBS1, γH2AX, and α-tubulin as loading control. In the presence of HA-ER-I-PpoI, phosphorylated Sp1 is recruited to the sites of the DSB (FIGS. 12A and B). Interestingly, the I-Ppo1 site in the Chrm1 locus contains three Sp1 binding sites and shows more localization of $γSp1^{101}$ to the this break site as compared to the rRNA break site (FIG. 12A vs. 12B). Since the rDNA sequence where I-PpoI cuts does not contain Sp1 binding sites, this suggests that Sp1 is recruited to the DSB sites.

Figure 13:
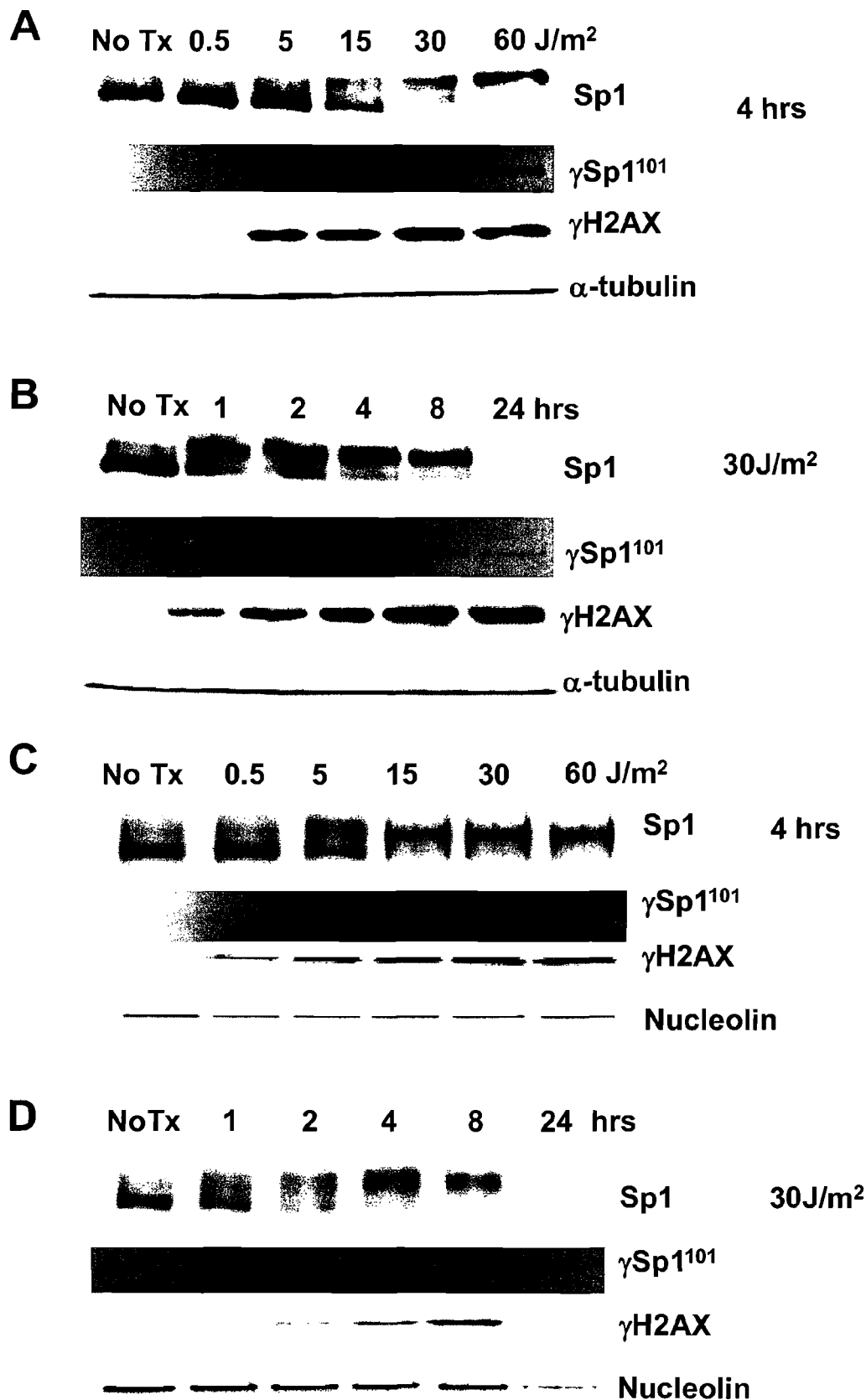
FIG. 13, comprising

Experiment #12:

To determine if Sp1 phosphorylation was stimulated by a wider range of DNA damage, NHDF and U2OS cells were exposed to ultra-violet light. UV light consists of shortwave energy in the form of UV-A (320-400 nm), UV-B (280-320 nm) and UV-C (200-280 nm). These wavelengths cause the formation of two main structural aberration in DNA, cyclobutane pyrimidine dimer (CPD) and 6-4 photoproducts (6-4 PPs). NHDF and U2OS cells were exposed to varying doses of UV-C (254 nm) in a Stratalinker and total cell lysates were prepared after four hours FIG. 13 A and 13C). With increasing doses of UV, Sp1 begins to shift to 105 kDa form in a dose dependent manner at 15 J/m², with the 105 kDa form becoming the predominate species at 30 J/m (FIGS. 13A and 13C, top panel). However, phosphorylation of Sp1 at serine 101 ($γSp1^{101}$) was detected when NHDF and U2OS cells were exposed to 5 J/m² UV (FIGS. 13A and 13C, second panel). This demonstrates that although the overall protein does not visually become phosphorylated as detected by the 10 kDa shift in electrophoretic mobility, phosphorylation of Sp1 still occurs at lower levels of damage. Immunoblot analysis of phosphorylated histone variant H2AX was determined as a marker for UV-induced damage (H2AX is phosphorylated in response to repair intermediates) and activation of the PI3-like kinase, ATR (Fernandez-Capetillo, DNA Repair (Amst), 2004, 3:959-67). γH2AX is also phosphorylated in a dose dependent manner in response to UV (FIG. 13A).

The kinetics of phosphorylation of Sp1 in response to ultra-violet light was next examined. NHDFs and U2OS cells were exposed to 30 J/m² of UV and lysates were prepared at various time points. A partial shift in Sp1 from the 95 kDa form to the 105 kDa was observed one hour after exposure to UV, with a complete shift occurring at 2-4 hours (FIGS. 13B and 13D, top panel).

Experiment #13

Figure 14:
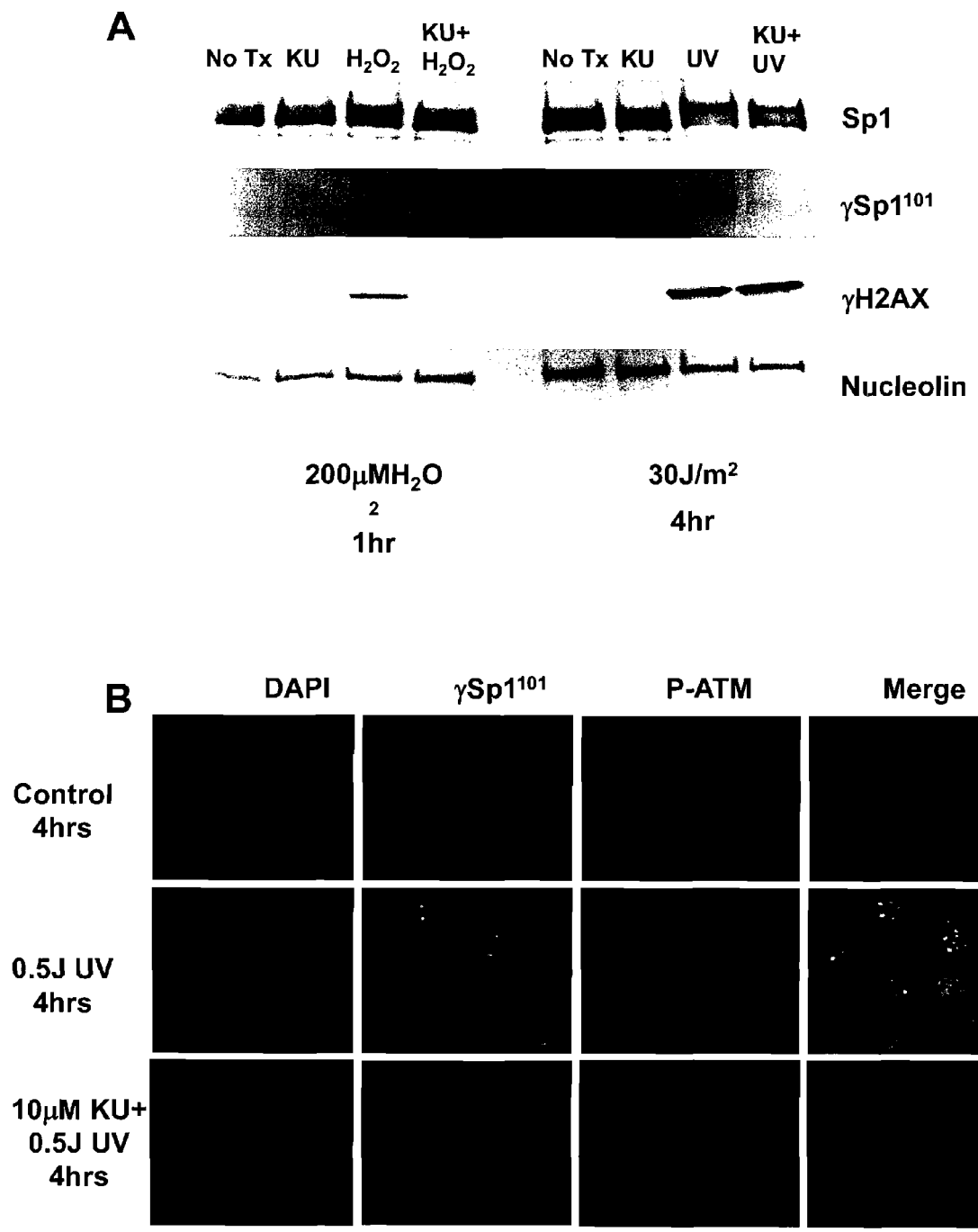
FIG. 14, comprising FIGS. 14A and 14B, demonstrates that UV-induced phosphorylation of Sp1 at S101 is ATM-dependent.

To further verify that Sp1 phosphorylation at serine 101 is ATM-dependent, U2OS cells were pretreated with 10 μM ATM inhibitor and exposed to either 200 μM $H_2O_2$ for one hour or 30 J/m² of UV for four hours. Pre-treatment with the ATM inhibitor blocked the electromobility shift in Sp1 from the 95 kDa to 105 kDa form and abolished the phosphorylation at serine 101 in response to $H_2O_2$ as described previously Olofsson et al., 2007, Mol. Cancer. Res. 5: 1319-30). The ATM inhibitor also abolished the phosphorylation of Sp1 at serine 101 in response to UV as well as resulted in a partial reduction of the overall electromobility shift seen with total Sp1 (FIG. 14A, top panel last lane). The phosphorylation of H2AX was diminished in cells exposed to the ATM inhibitor and $H_2O_2$ but not in cells treated with the ATM inhibitor and UV as seen in FIG. 14A. H2AX is known to be phosphorylated by ATM in response to double strand breaks (Rogakou, et al. 1998, J. Biol. Chem. 273:5858-68) and ATR in response to UV (Ward, et al. 2001, J. Biol. Chem. 276:47759-62). Phosphorylation of H2AX has been shown not to be affected by the ATM inhibitor after exposure to UV (Hickson, et al. 2004, Cancer Res. 64:9152-9). U2OS cells were exposed to 0.5 J/m² of UV and immunofluorescence was done with antibodies directed to phospho-ATMs1981 and γSp1[101]. FIG. 14B (middle row) demonstrates that after exposure to UV, ATM is phosphorylated on serine 1981 and co-localizes with the γSp1[101]. When cells are incubated with the ATM inhibitor (KU55933) before treatment of UV, ATM is still phosphorylated at serine 1981 as previously shown by ATR, but the kinase activity of the protein is inhibited by KU55933 (Hickson et al., 2004, Cancer Res. 64:9152-9).] This inhibition of ATM kinase activity is demonstrated by the lack of γSp1[101] in cells pre-treated with ATM inhibitor (FIG. 14C, bottom row).

Experiment #14

Figure 15:
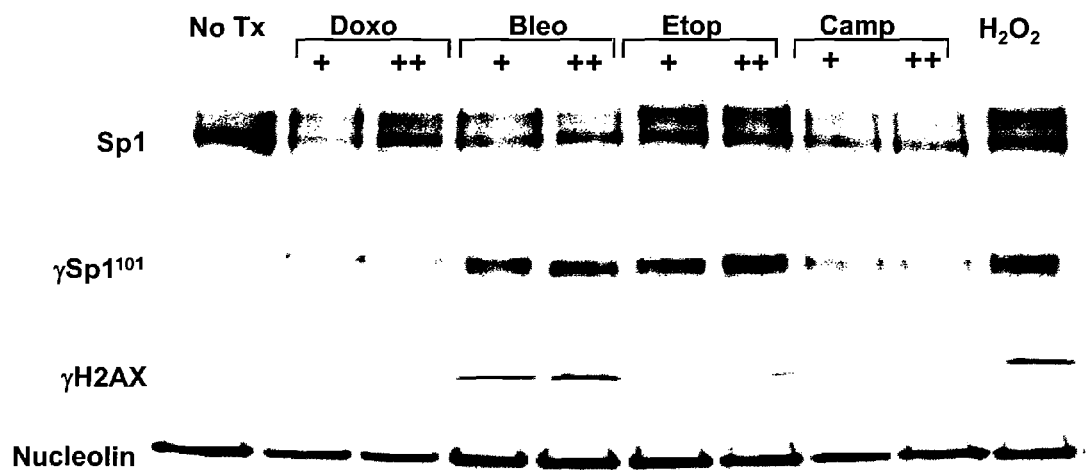
FIG. 15, comprising
Figure 15:
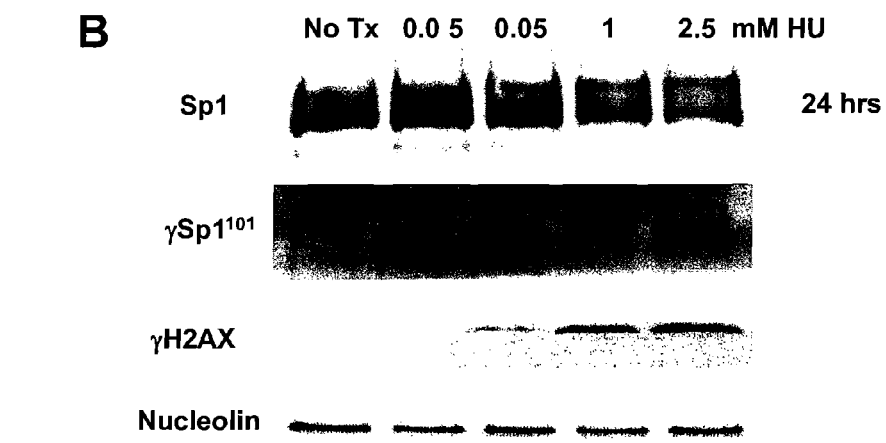
Figure 15:
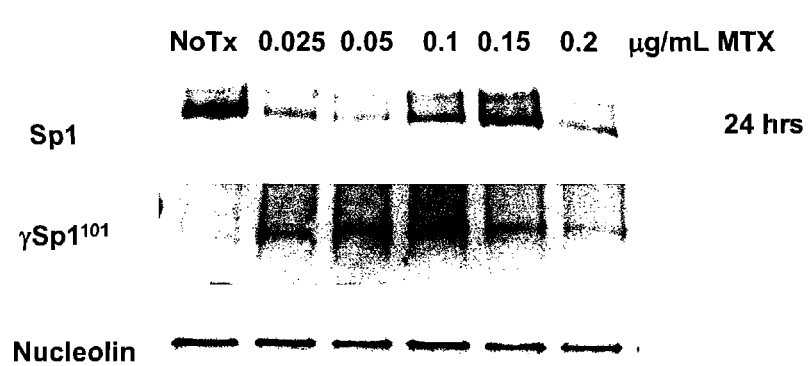

To further establish the validity of phosphorylation of Ser101 as a marker of DNA damage, U2OS cells were treated with a variety of DNA damaging agents used in cancer treatment followed by immunoblot of cell lysates with Sp1, γSp1[101], γH2AX and αtubulin. U2OS cells were exposed to low and high dose chemotherapeutic agents (+ for low or ++ for high). The concentrations were 5 and 15 μM doxorubicin (Doxo), 50 and 100 μg/ml Bleomycin (Bleo), 5 and 10 μM Etopsoide (Etop), 5 and 20 μM Camptothecin (Camp), and 200 μM $H_2O_2$ for 1 hour (FIG. 15A). Sp1 phosphorylation at Ser101 was also observed in U2OS cells treated with varying concentrations of hydroxyurea (HU) (FIG. 15B) or methotrexate (MTX) (FIG. 15C); cells were harvested 24 hours after treatment with the drugs. There was no visualization of H2AX phosphorylation in cells exposed to methotrexate. The phosphor-serine 101 Sp1 antibody was able to detect DNA damage at lower levels of damage, i.e. lower doses of damaging agent than γH2AX, particularly damage resulting from etoposide and doxorubicin, as well as that resulting from treatment with the antimetabolites, hydroxyurea or methotrexate.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An antibody that specifically binds to the polypeptide of SEQ ID NO: 2 having a phosphate moiety at serine residue 101 relative to SEQ ID NO: 2.

2. The antibody of claim 1, wherein said antibody is a polyclonal antibody, or fragment thereof.

3. The antibody of claim 1, wherein said antibody is a monoclonal antibody, or fragment thereof.

4. The antibody of claim 1, wherein said antibody comprises a detectable label.

5. The antibody of claim 4, wherein said detectable label is selected from the group consisting of a radioactive, a fluorescent, a biological and an enzyme label.

* * * * *

UNITED STATES PATENT AND TRADEMARK OFFICE
CERTIFICATE OF CORRECTION

PATENT NO. : 8,476,025 B2
APPLICATION NO. : 12/187187
DATED : July 2, 2013
INVENTOR(S) : Jane Clifford, Beatrix A. Olofsson and Crystal M. Kelly Page 1 of 1

It is certified that error appears in the above-identified patent and that said Letters Patent is hereby corrected as shown below:

In the Specification

In Column 1, lines 7 through 13, delete the paragraph and replace with the following paragraph:

-- STATEMENT REGARDING FEDERALLY SPONSORED RESEARCH OR DEVELOPMENT

This invention was made, in part, with government support under Grant No. CA91681 awarded by the National Institutes of Health. The government has certain rights in the invention. --

Signed and Sealed this
Fifth Day of November, 2013

Teresa Stanek Rea
*Deputy Director of the United States Patent and Trademark Office*

SEQUENCE LISTING

```
<160> NUMBER OF SEQ ID NOS: 16

<210> SEQ ID NO 1
<211> LENGTH: 7667
<212> TYPE: DNA
<213> ORGANISM: Homo sapiens

<400> SEQUENCE: 1
gtccgggttc gcttgcctcg tcagcgtccg cgttttcccc ggcccccccc aaccccccg      60 gacaggaccc ccttgagctt gtccctcagc tgccaccatg agcgaccaag atcactccat     120
ggatgaaatg acagctgtgg tgaaaattga aaaaggagtt ggtggcaata atgggggcaa    180
tggtaatggt ggtggtgcct tttcacaggc tcgaagtagc agcacaggca gtagcagcag    240
cactggagga ggagggcagg agtcccagcc atccccttttg gctctgctgg cagcaacttg    300
cagcagaatt gagtcaccca atgagaacag caacaactcc cagggcccga gtcagtcagg    360
gggaacaggt gagcttgacc tcacagccac acaactttca cagggtgcca atggctggca    420
gatcatctct tcctcctctg gggctacccc tacctcaaag gaacagagtg gcagcagtac    480
caatggcagc aatggcagtg agtcttccaa gaatcgcaca gtctctggtg ggcagtatgt    540
tgtggctgcc gctcccaact tacagaacca gcaagttctg acaggactac ctggagtgat    600
```

```
gcctaatatt cagtatcaag taatcccaca gttccagacc gttgatgggc aacagctgca    660
gtttgctgcc actggggccc aagtgcagca ggatggttct ggtcaaatac agatcatacc    720
aggtgcaaac caacagatta tcacaaatcg aggaagtgga ggcaacatca ttgctgctat    780
gccaaaccta ctccagcagg ctgtccccct ccaaggcctg gctaataatg tactctcagg    840
acagactcag tatgtgacca atgtaccagt ggccctgaat gggaacatca ccttgctacc    900
tgtcaacagc gtttctgcag ctaccttgac tcccagctct caggcagtca cgatcagcag    960
ctctgggtcc caggagagtg gctcacagcc tgtcacctca gggactacca tcagttctgc   1020
cagcttggta tcatcacaag ccagttccag ctccttttc accatgcca atagctactc    1080 aactactact accaccagca acatgggaat tatgaacttt actaccagtg atcatcagg   1140 gaccaactct caaggccaga caccccagag ggtcagtggg ctacagggg ctgatgctct   1200 gaacatccag caaaccaga catctggagg ctcattgcaa gcaggccagc aaaaagaagg   1260
agagcaaaac cagcagacac agcagcaaca aattcttatc cagcctcagc tagttcaagg   1320
gggacaggcc ctccaggccc tccaagcagc accattgtca gggcagacct ttacaactca   1380
agccatctcc caggaaaccc tccagaacct ccagcttcag gctgttccaa actctggtcc   1440
catcatcatc cggacaccaa cagtggggcc caatggacag gtcagttggc agactctaca   1500
gctgcagaac ctccaagttc agaacccaca agcccaaaca atcaccttag ccccaatgca   1560
gggtgtttcc ttggggcaga ccagcagcag caacaccact ctcacaccca ttgcctcagc   1620
tgcttccatt cctgctggca cagtcactgt gaatgctgct caactctcct ccatgccagg   1680
cctccagacc attaacctca gtgcattggg tacttcagga atccaggtgc acccaattca   1740
aggcctgccg ttggctatag caaatgcccc aggtgatcat ggagctcagc ttggtctcca   1800 tgggctggt ggtgatggaa tacatgatga cacagcaggg ggagaggaag gagaaaacag   1860
cccagatgcc caaccccaag ccggtcggag gacccggcgg gaagcatgca cctgccccta   1920
ctgtaaagac agtgaaggaa ggggctcggg ggatcctggc aaaaagaaac agcatatttg   1980
ccacatccaa ggctgtggga aagtgtatgg caagacctct cacctgcggg cacacttgcg   2040
ctggcataca ggcgagaggc catttatgtg tacctggtca tactgtggga aacgcttcac   2100
acgttcggat gagctacaga ggcacaaacg tacacacaca ggtgagaaga atttgcctg   2160 ccctgagtgt cctaagcgct tcatgaggag tgaccacctg tcaaaacata tcaagaccca   2220
ccagaataag aagggaggcc caggtgtagc tctgagtgtg ggcactttgc ccctggacag   2280
tggggcaggt tcagaaggca gtggcactgc cactccttca gcccttatta ccaccaatat   2340
ggtagccatg gaggccatct gtccagaggg cattgcccgt cttgccaaca gtggcatcaa   2400
cgtcatgcag gtggcagatc tgcagtccat taatatcagt ggcaatggct ctgagatca   2460 ggcacccggg gccagagaca tatgggccat acccctttaac cccgggatgc aaggtagcat   2520
gggtccaaga gacatggaag agagagccat gaagcattaa aatgcatggt gttgagaaga   2580
atcaggagag ggatacaaga gaggagatgg ggtcccggca cccatctgta tcatcagtgc   2640
ctctttgaag gtgggaaaca ttagtgaaaa ttctgttggt gccacgcttt gatgagcatt   2700
tgtttgaccc cagtttcttc ttacacttct taccccagcc tacccttcct gcatttctct   2760
tctcagctct tccatgatgg attccccccc ctttcctaaa gccatcatgc cttgataaat   2820
atatatgatc attgaaatac ttttttaacaa aaaacagatt ctatattatt atatatatat   2880
atatatatat aaagatatat agagatgcat tcacaggggt tggctgggag gaggaagacc   2940
attctgtgac caaaatacct tggtcatttt ttttatattg ccttatttcc ctatggctga   3000
```

```
gccttgttgt gacacatcaa gctttctgt agatgttgtc ttggcttccc accagcttaa      3060
gcgttcatat gctctgcttt tagttcatat atacatacat aatgttttc ctttcttaat      3120 tttgtctttt tgtttgggat cagcttcttg cactccttcc ctaactcaac tgttgccgtc      3180
tcatcttctc tcatctgatc acttcatgtt ttgttttgt tactgcctgg atgaggcact      3240
tctgtcaatt ttttcaggac cttagttcca gcagcagaat ggaaaaatcc ttgaagccca      3300
ggctgatgct tgaagtaact gtggagggag tgttcaaaat actactgacg caggcacctt      3360
cttggcgctg gagagtcaaa ggcatctccc ttcattagct gctctgagca tcaagaatta      3420
gaagtctttc agtggaattg tacaagagtc cctttgaaga taataatctt ggctcagttt      3480
gtataaactg tcaaattttc aaataatagg tagggggctt tcactaggaa aatcatgtgc      3540
tcagaagagg aaatgactcg tagtcaggtt caggagttag tggagtattt ggactttggt      3600
actgctgtct tccaaggtag ctctaagttt tgatgtgtgg gcttctgagt ttatattctg      3660
aaaggaaata cacttctttt gaacatcccc actaggttct tttccattgt caataaggag      3720
catcagccag tgaatctgtt tcaggtttcc attctgcaga actcctccaa agcatgtgct      3780
agtggcaaga cagtggttct tatgatgttt tcccttaact tttccttgta tgttcttggg      3840
tggttcctaa gggaaaggga agcacatgat catgggaatg atagcccaga acaaaaagaa      3900
atcttgtctt accacagtgt tttataggag agattgggag aaatcatcct gtttctctg       3960 tgacctgatt tcagaagaga ctgatccaaa aattataacg gcagggaacc tagtgcattt      4020
ggcactgaga tttaaatgca accagaattg tcctcaaggc ccagccataa aagcattgtc      4080
tctctcgacc ttctggtatc ttgttagaga gcttttcact gtgaggaagt gtggaaaaat      4140
agctctgtgt gtgtgtgtgt gtgtgtgtgt gtgtgtgt gtaatctgtt aggttgggga       4200
taggttttct gctagccaat attaaaagag acctgcaata aaaaaattac cctgatctga      4260
tagaaagcaa gtgtttttgt atgtgtgggt gaatgtgtgt tcatgcccgt atatgtctac      4320
acacagatga caaattatat ttgaaatcgt tggaaaataa attcagatca aaatgccttt      4380
caggcccatt acctagaaat ctatcttaaa acctgggtat gttcctaagg tcatttcttt      4440
gcttatgcta aattaattac aattatgaat ggaggatatt ctactgtact ttttaaaaa      4500 gaaactattt ttgtgtttga aagtgaaacc aacatccaga tctatagcag agtccttatt      4560
cttctcataa atcttttac tttggctaca aatagatgat ggtatgattc tattatatat      4620
tttatataaa atccatccaa attaagtttt gggtaagtgt gttgtttaat ctgaactata      4680
gtaacttaat actctaaaca atagttcact ccatttggtc cttcctccac agatgtaatt      4740
atgttttcaa ctcaggaact atggcaagga actttcccca gatcaaattc tattaacgct      4800
gagatacaag tcatccatgc acagccacta tcatacccctt tattctcact gaaaggcaga      4860
actcagaacc tgttatttta tgtctgtaat catgtacttt ggcatctttt ggaggaaagg      4920
ggcaggataa ctcactggaa tgtacagtat tttgctagtg catttcaagg aatggaatct      4980
tctccagtat gaaattacca gatataaaat aatgtaatga tgctgaggat ataagctttt      5040
agaaggtaat ttgatggtat ttcttttctcg aatgaaaagc tgctggttta ccctcaaccc      5100
tattcattag cattaccatg agtgaattta tatctaatta tttccacttg ccctgttctc      5160
ttcacaccaa ggaagctcca gatccagtat cttgtttggc ctcaaaacag aagcagcttc      5220
ttttgtctcc cagcagtagt gagccactca gtctcttcca caggaagttt ggagcctaca      5280
ttccttgagt caggagctta ttacagaaaa accccgtttc cctgaacttt tggctaacag      5340
```

```
aaattaattt aactgacatg catattgatt ctgaaatttt tttcctaagt ttttttcatt    5400
tttttgaatg agttttttaa atttttagg tgaccaaaac ttgcagggca ggggatgccc    5460
agaagagtgg tgagatagta aaacacttat tccctcatcc tttcaggttt tcaggttgcc    5520
catttatatt catttacatg tcatttgact gtctcacttt ttacccagaa cagtaacaac    5580
ccacaccgtc ttccttcagg gatttccaac tggcactctg tgggtgctac acagaatgca    5640
atttaatgga tatttctcag cctggttcag aataaattga tcctttgatc cagaaagta    5700 tatactgaag tgtgggataa agattatgat taggggaggg ttggagacaa agctgtaaa    5760 ttactatggc tgatttattt ctactatata catatatatt ttttgctttt gtatatccta    5820
tataggaaac taagcattgt atttttttta acaaatctaa aaaagcacta tgaactacag    5880
gtgtttgact ttcaaaatat attttgtatt gttaatatct tcacattgtg tgaatactgg    5940
aagctgcaga tctttgctag gacgcaataa atttatatac ttttttgaggg gttcttctgg    6000 ggtgctaatc aggcccctgt tatgcttagg gggagccctg tgctacttg cttgaagttt    6060 tcagtgtaag taccctgatg ccttttggac cttgggatca gatcaagagt tttggagatc    6120
aggtaccaag gaaataagga cagtctagct gcctcaagtg aggggccctt tgcatagctc    6180
tccttccccc tcactgaagc tgggtagcct attggggttg agagggaaaa tgtgaaatct    6240
cagaatttat ctcccttaga agagagccag taactatgt acaaggatga agaaaggtc    6300 gcagcagtag ctttgggaa agggaggaag atatggcact tctccaaccc cggaaaacat    6360
tgcttttgaa aactgctgat aaaatatgag ccggttatta cttctgtttg ggagactgtg    6420
ctctctgtgg tgcctctctt ggctctactc cacagatacc agacctcttc taagaggatg    6480
agcagaccag ctttgaggtt gacctgtttc tctttgtctg ccttcccaaa acaccagccc    6540
ccaggaagac attaagcagc cttaagctta aattcctact ccctcttcca aatttggctc    6600
acttgcctta gatccaaggc agggaaagga aaagaagggg ggtctctggc tttattactc    6660
ccctaagtct ttactctgac ttccccaaac ccagaaagat tttctccaca gtgttcattt    6720
gaaagaggag tattttgtcc cattttcccc ttcctcatta tcaaacagcc ccagtcttcc    6780
ttgtctctgc taagaaagta gaggcatgat gatctgcctc tcaactgccc taagtcctag    6840
ctaagtatca ggggaaaaaa aaaaaaaaaa agcctaacaa atgggattag actagggctg    6900
caagtagtga ggattttgtt gatacctctg ctgggatgtg tgctttccca tatcttgcct    6960
tcaggaatta cactgtgcct ttccccagg gatatgggct ctgtctaccc agtgctccag    7020
tttcccggta actgctcttg aacattgtgg acaagggcag gtcttcatat ttttgatcat    7080
ccctttctcc cagtgaaatc ccatagccct tacctagagt ctagggcaca aagacttcgg    7140
ggaagataca ctgagattga cctgaggaga catctacaca caccagtggc agctgcccca    7200
gggcctgctt cccttcctta agtctgtcat cctctggaag ggatgggtgg tgctccaatc    7260
tctggtgcct aaaaacccaa gtttatttct ctcttaacac tggcaataac cagtccacac    7320
cactgttgcc ttttaaaacc tcttaataat ctcatgctgt gtttgttttg attccaatcc    7380
aattatcacc agggctgtgt gggtaaatgc ttttaaatgc tctctcatct tgttcttccc    7440
cctcaccccc cactcttagg tatgtatgat gctaatcttg tccctaagta agtttcttcc    7500
tgctcctttt gtatcttcct ttcttgtctt tcctcctacc ttttgtctct tggtgttttg    7560
ggactttttt ttttttttttt ttggcctttt gtacaaagat tagtttcaat gtagtctgta    7620
gcctcctttg taaaccaatt aaaaagtttt ttaataaaaa aaaaaaa           7667
```

<210> SEQ ID NO 2
<211> LENGTH: 785
<212> TYPE: PRT
<213> ORGANISM: Homo sapiens

<400> SEQUENCE: 2

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Thr Gly Ser Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380

```
Gln Lys Glu Gly Glu Gln Asn Gln Gln Thr Gln Gln Gln Ile Leu
385                 390                 395                 400

Ile Gln Pro Gln Leu Val Gln Gly Gly Gln Ala Leu Gln Ala Leu Gln
            405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
            435                 440                 445

Ile Ile Ile Arg Thr Pro Thr Val Gly Pro Asn Gly Gln Val Ser Trp
450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
            485                 490                 495

Ser Ser Asn Thr Thr Leu Thr Pro Ile Ala Ser Ala Ala Ser Ile Pro
            500                 505                 510

Ala Gly Thr Val Thr Val Asn Ala Ala Gln Leu Ser Ser Met Pro Gly
            515                 520                 525

Leu Gln Thr Ile Asn Leu Ser Ala Leu Gly Thr Ser Gly Ile Gln Val
530                 535                 540

His Pro Ile Gln Gly Leu Pro Leu Ala Ile Ala Asn Ala Pro Gly Asp
545                 550                 555                 560

His Gly Ala Gln Leu Gly Leu His Gly Ala Gly Gly Asp Gly Ile His
            565                 570                 575

Asp Asp Thr Ala Gly Gly Glu Glu Gly Glu Asn Ser Pro Asp Ala Gln
            580                 585                 590

Pro Gln Ala Gly Arg Arg Thr Arg Arg Glu Ala Cys Thr Cys Pro Tyr
            595                 600                 605

Cys Lys Asp Ser Glu Gly Arg Gly Ser Gly Asp Pro Gly Lys Lys Lys
610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
            645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
            675                 680                 685

Pro Glu Cys Pro Lys Arg Phe Met Arg Ser Asp His Leu Ser Lys His
            690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
            725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
            755                 760                 765

Val Met Gln Val Ala Asp Leu Gln Ser Ile Asn Ile Ser Gly Asn Gly
            770                 775                 780

Phe
785
```

<210> SEQ ID NO 3
<211> LENGTH: 37
<212> TYPE: DNA
<213> ORGANISM: Artificial
<220> FEATURE:
<223> OTHER INFORMATION: Chemically synthesized

<400> SEQUENCE: 3
cctcacagcc acacaacttg cacagggtgc caatggc                           37

<210> SEQ ID NO 4
<211> LENGTH: 41
<212> TYPE: DNA
<213> ORGANISM: Artificial
<220> FEATURE:
<223> OTHER INFORMATION: Chemically synthesized

<400> SEQUENCE: 4
acctcacagc cacacaactt gaacagggtg ccaatggctg g                      41

<210> SEQ ID NO 5
<211> LENGTH: 26
<212> TYPE: DNA
<213> ORGANISM: Artificial
<220> FEATURE:
<223> OTHER INFORMATION: Chemically synthesized

<400> SEQUENCE: 5
gcagctctgg ggcccaggag agtggc                                       26

<210> SEQ ID NO 6
<211> LENGTH: 29
<212> TYPE: DNA
<213> ORGANISM: Artificial
<220> FEATURE:
<223> OTHER INFORMATION: Chemically synthesized

<400> SEQUENCE: 6
cccaggagag tggcgcacag cctgtcacc                                    29

<210> SEQ ID NO 7
<211> LENGTH: 33
<212> TYPE: DNA
<213> ORGANISM: Artificial
<220> FEATURE:
<223> OTHER INFORMATION: Chemically synthesized

<400> SEQUENCE: 7
ggtggtggtg cctttgcaca ggctcgaagt agc                               33

<210> SEQ ID NO 8
<211> LENGTH: 25
<212> TYPE: DNA
<213> ORGANISM: Artificial
<220> FEATURE:
<223> OTHER INFORMATION: Chemically synthesized

<400> SEQUENCE: 8
ggagggcagg aggcccagcc atccc                                        25

<210> SEQ ID NO 9
<211> LENGTH: 30
<212> TYPE: DNA
<213> ORGANISM: Artificial
<220> FEATURE:
<223> OTHER INFORMATION: Chemically synthesized

```
<400> SEQUENCE: 9
gccagcttgg tatcagcaca agccagttcc                                    30

<210> SEQ ID NO 10
<211> LENGTH: 33
<212> TYPE: DNA
<213> ORGANISM: Artificial
<220> FEATURE:
<223> OTHER INFORMATION: Chemically synthesized

<400> SEQUENCE: 10
cctttacaac tcaagccatc gcccaggaaa ccc                                33

<210> SEQ ID NO 11
<211> LENGTH: 50
<212> TYPE: DNA
<213> ORGANISM: Artificial
<220> FEATURE:
<223> OTHER INFORMATION: Chemically synthesized

<400> SEQUENCE: 11
gaacagcaac aacgcccagg gcccggctca gtcaggggga acaggtgagc               50

<210> SEQ ID NO 12
<211> LENGTH: 19
<212> TYPE: RNA
<213> ORGANISM: Artificial
<220> FEATURE:
<223> OTHER INFORMATION: Chemically synthesized

<400> SEQUENCE: 12
ucaguggaau uguacaaga                                                19

<210> SEQ ID NO 13
<211> LENGTH: 19
<212> TYPE: RNA
<213> ORGANISM: Artificial
<220> FEATURE:
<223> OTHER INFORMATION: Chemically synthesized

<400> SEQUENCE: 13
ggaaucuucu ccaguauga                                                19

<210> SEQ ID NO 14
<211> LENGTH: 14
<212> TYPE: PRT
<213> ORGANISM: Artificial
<220> FEATURE:
<223> OTHER INFORMATION: Chemically synthesized
<220> FEATURE:
<221> NAME/KEY: Xaa
<222> LOCATION: (8)..(8)
<223> OTHER INFORMATION: where Xaa represents [pS], a phosphorylated
      serine residue
<220> FEATURE:
<221> NAME/KEY: Xaa
<222> LOCATION: (14)..(14)
<223> OTHER INFORMATION: where Xaa represents K-amide

<400> SEQUENCE: 14

Asp Leu Thr Ala Thr Gln Leu Xaa Gln Gly Ala Asn Gly Xaa
1               5                   10

<210> SEQ ID NO 15
<211> LENGTH: 19
<212> TYPE: RNA
<213> ORGANISM: Artificial
```

```
<220> FEATURE:
<223> OTHER INFORMATION: Chemically synthesized

<400> SEQUENCE: 15
ggaaucuucu acaguauga                                                    19

<210> SEQ ID NO 16
<211> LENGTH: 15
<212> TYPE: DNA
<213> ORGANISM: Artificial
<220> FEATURE:
<223> OTHER INFORMATION: Chemically synthesized

<400> SEQUENCE: 16
ctctcttaag gtagc                                                        15
```